(12) United States Patent
Murase et al.

(10) Patent No.: US 10,809,255 B2
(45) Date of Patent: Oct. 20, 2020

(54) SPECIMEN MEASUREMENT APPARATUS

(71) Applicant: Toshiba Medical Systems Corporation, Otawara-shi (JP)

(72) Inventors: Naoko Murase, Saitama (JP); Isao Nawata, Yokohama (JP); Shoichi Kanayama, Otawara (JP)

(73) Assignee: CANON MEDICAL SYSTEMS CORPORATION, Otawara-shi (JP)

( * ) Notice: Subject to any disclaimer, the term of this patent is extended or adjusted under 35 U.S.C. 154(b) by 404 days.

(21) Appl. No.: 15/696,806

(22) Filed: Sep. 6, 2017

(65) Prior Publication Data
US 2018/0067112 A1  Mar. 8, 2018

(30) Foreign Application Priority Data

Sep. 6, 2016 (JP) ................. 2016-173643
Sep. 1, 2017 (JP) ................. 2017-168519

(51) Int. Cl.
*G01N 21/552* (2014.01)
*G01N 33/543* (2006.01)
*G01N 21/77* (2006.01)

(52) U.S. Cl.
CPC ..... *G01N 33/54373* (2013.01); *G01N 21/552* (2013.01); *G01N 21/77* (2013.01); *G01N 21/7703* (2013.01); *G01N 2201/08* (2013.01)

(58) Field of Classification Search
CPC .................. G01N 21/552; G01N 33/54373
See application file for complete search history.

(56) References Cited

U.S. PATENT DOCUMENTS

2012/0184048 A1 * 7/2012 Van Ommering ..........................
G01N 33/54313
436/164

FOREIGN PATENT DOCUMENTS

| EP | 0 357 786 | 3/1990 |
|---|---|---|
| JP | 2510551 | 6/1996 |
| JP | 2603843 | 4/1997 |
| JP | 2009-133842 | 6/2009 |
| JP | 4381752 | 12/2009 |
| JP | 2012-215553 | 11/2012 |
| JP | 2016-038218 | 3/2016 |

* cited by examiner

*Primary Examiner* — Jonathan M Hurst
(74) *Attorney, Agent, or Firm* — Oblon, McClelland, Maier & Neustadt, L.L.P.

(57) ABSTRACT

According to one embodiment, a specimen measurement apparatus includes a detector, a reaction promoter and processing circuitry. The detector generates an electrical signal based on a reactive state in a reaction chamber in which a mixture of a test substance and a reagent is contained. The reaction promoter supplies to the reaction chamber energy to promote reaction in the reaction chamber. The processing circuitry switches an energy supply state in accordance with a predetermined time schedule, determines a stationary state of the test substance based on an electrical signal generated after the energy supply state is switched, and outputs the stationary state obtained by the determination.

18 Claims, 11 Drawing Sheets

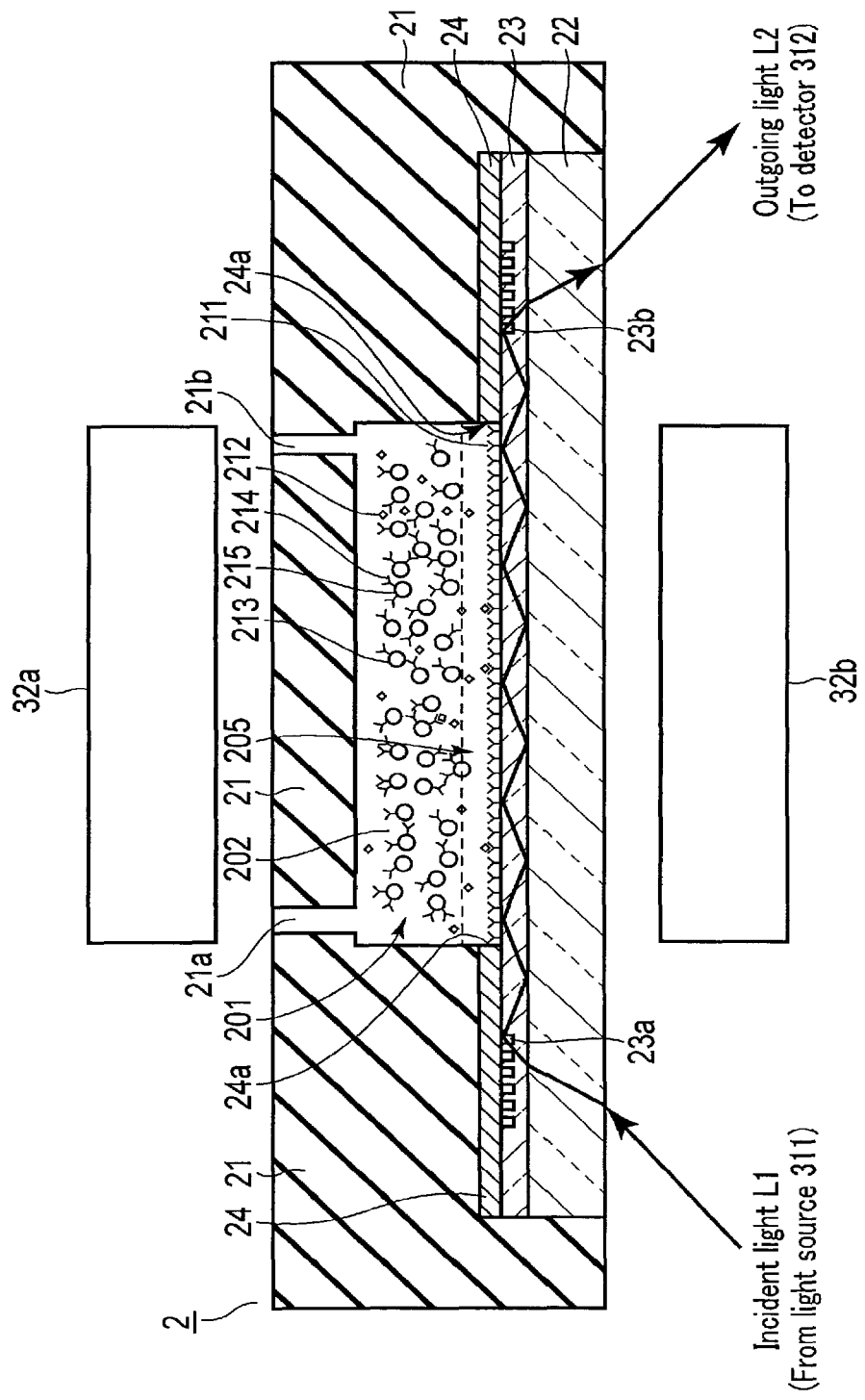
F I G. 2

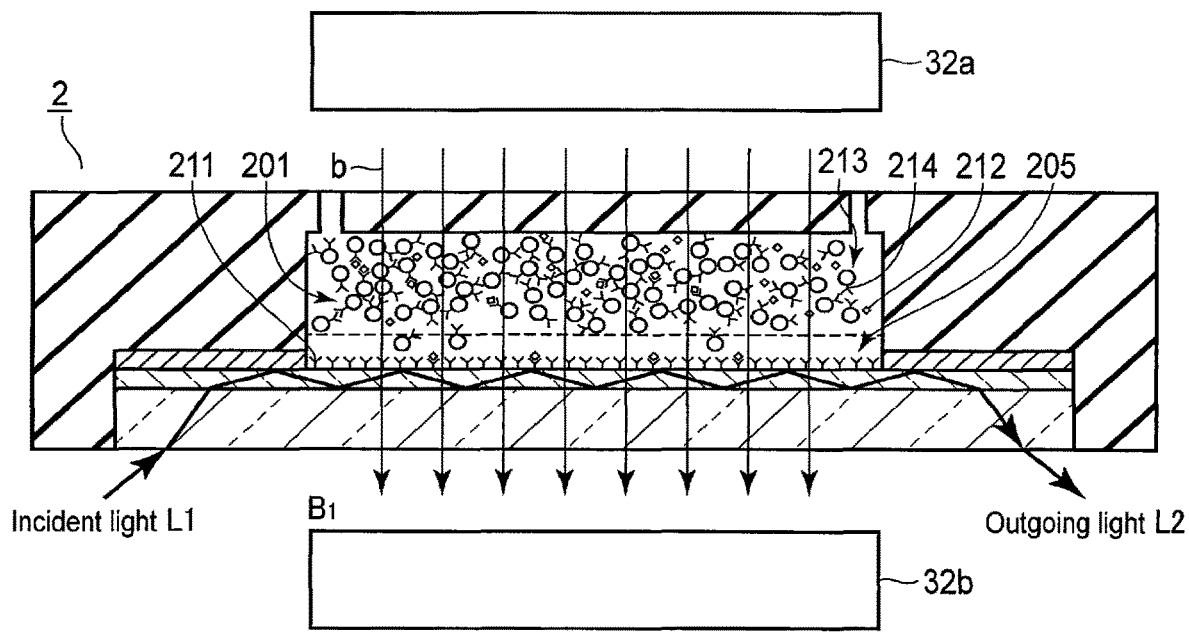
F I G. 6
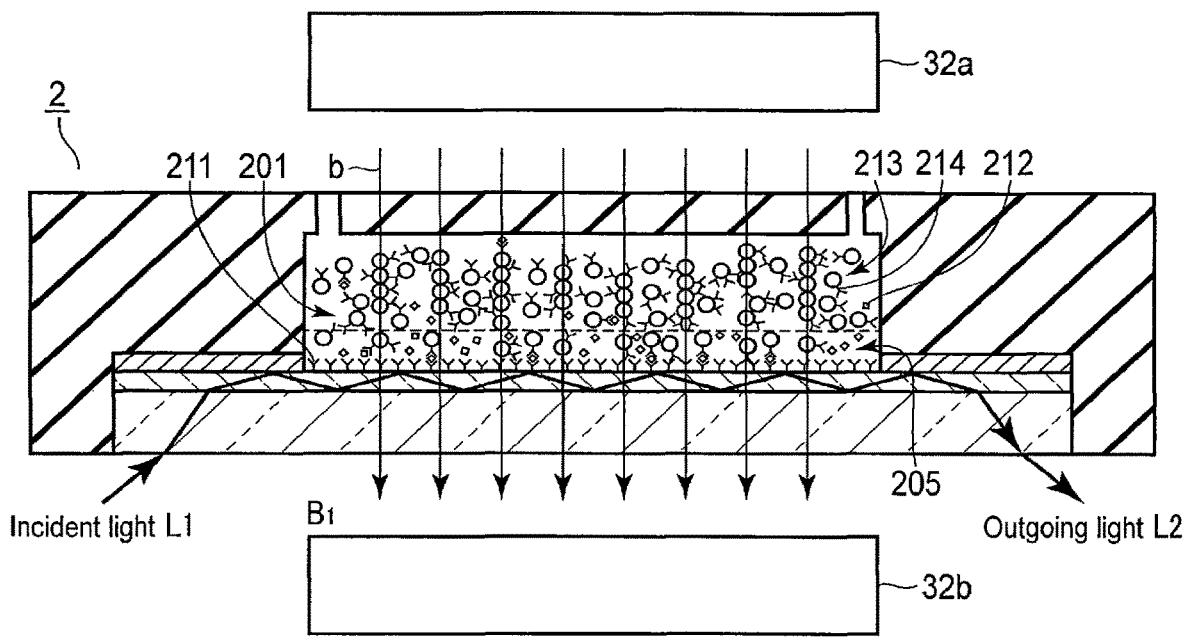
F I G. 7

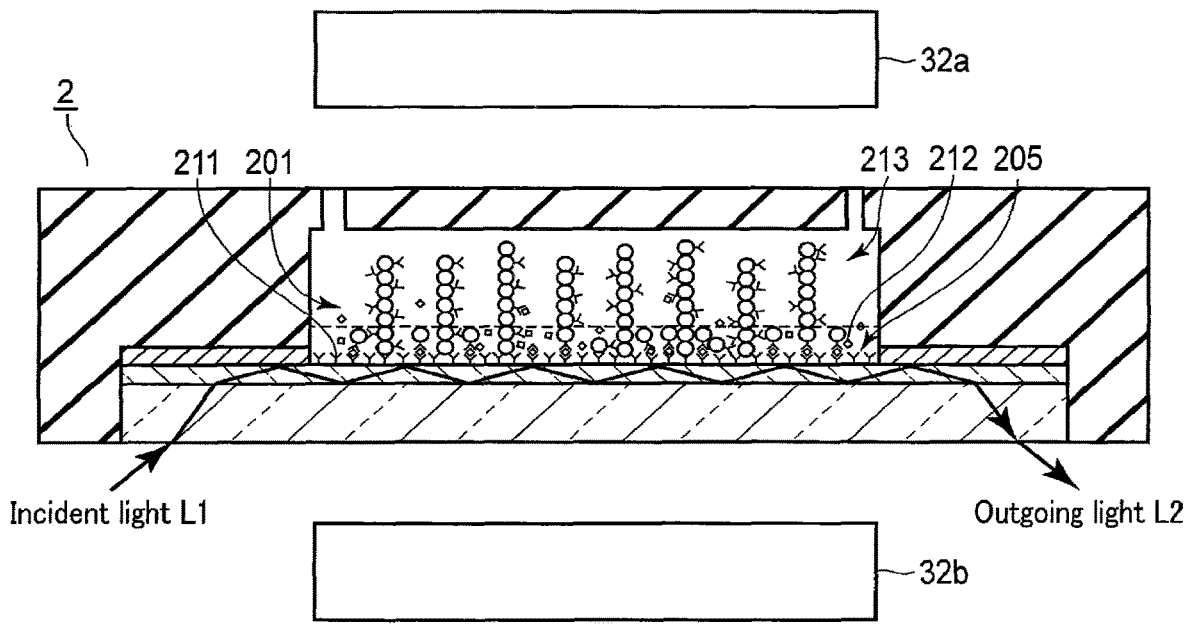
F I G. 10
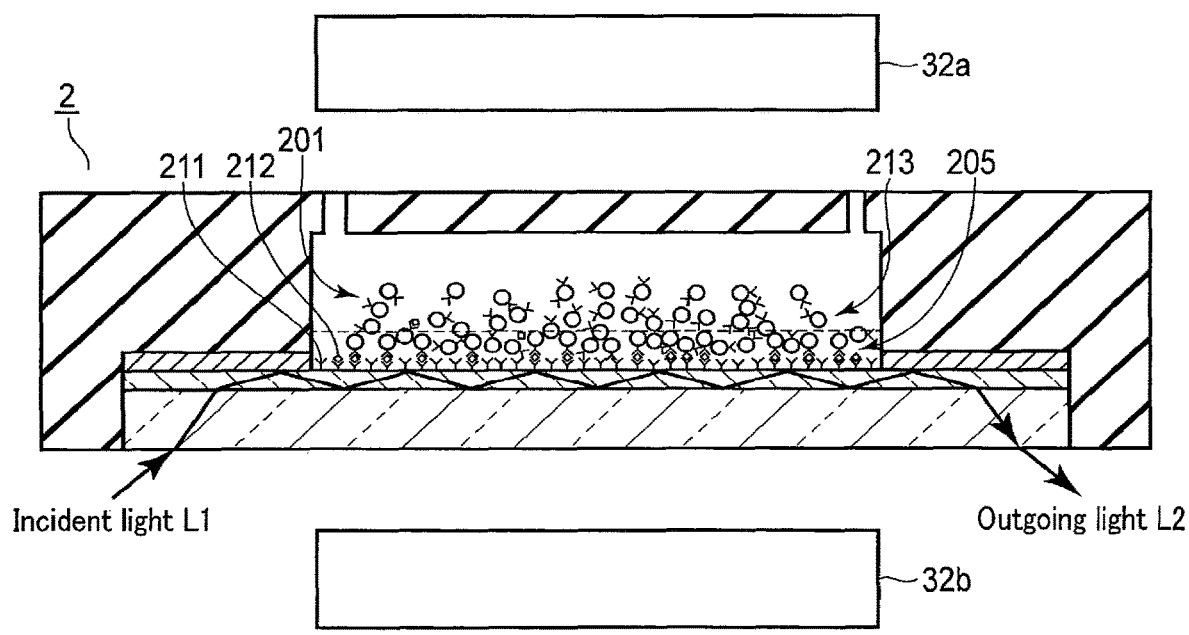
F I G. 11

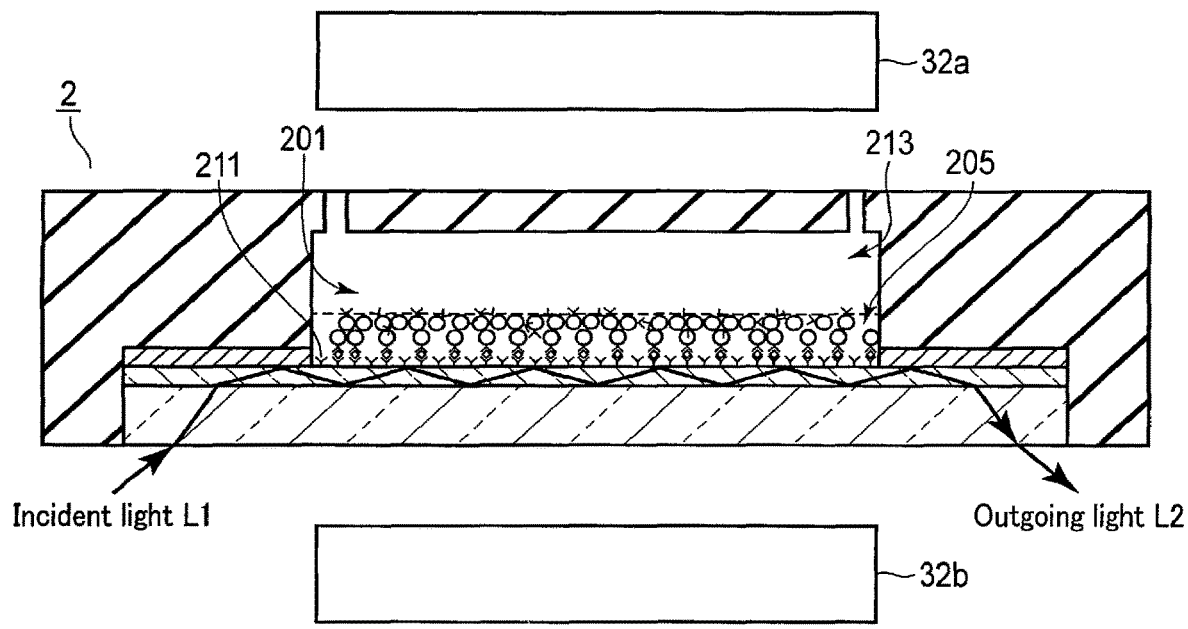
F I G. 12
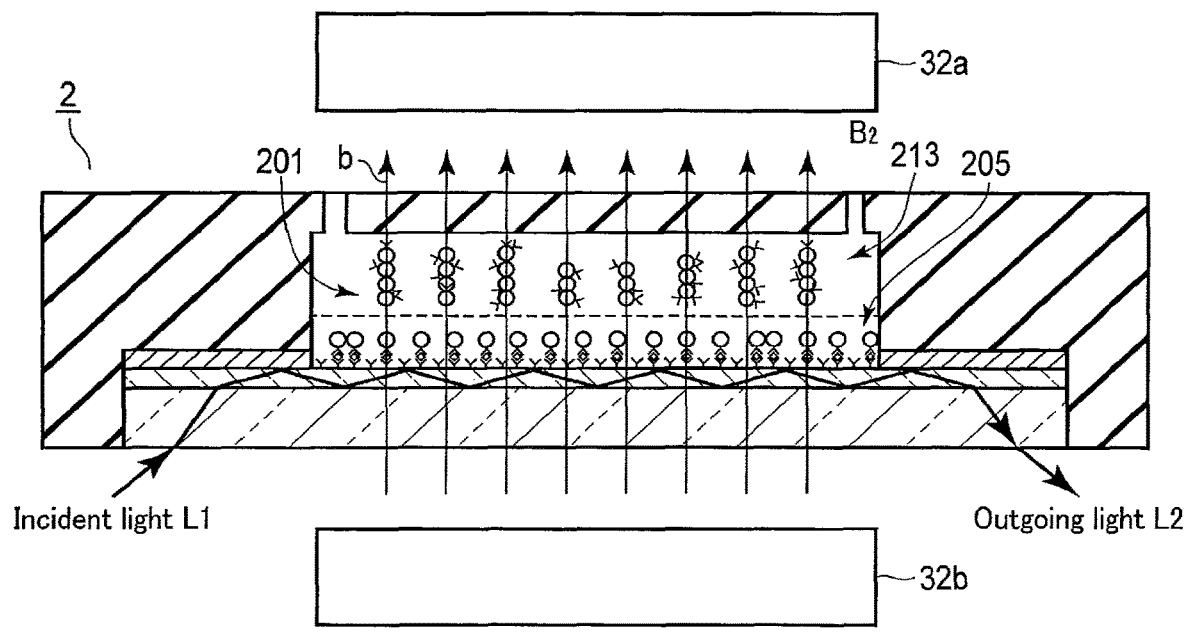
F I G. 13

SPECIMEN MEASUREMENT APPARATUS

CROSS-REFERENCE TO RELATED APPLICATIONS

This application is based upon and claims the benefit of priority from the prior Japanese Patent Application No. 2016-173643, filed Sep. 6, 2016, and No. 2017-168519, filed Sep. 1, 2017, the entire contents of both which are incorporated herein by reference.

FIELD

Embodiments described herein relate generally to a specimen measurement apparatus.

BACKGROUND

Specimen measurement apparatuses determine the presence or absence of a target substance in a specimen by measuring a measurement sample prepared by a specimen and a reagent using an optical or electrical method. In the specimen measurement apparatuses, an electrical signal is detected based on a reactive state in a vessel in which a mixture of a specimen and a reagent is contained, and the presence or absence of the target substance in the specimen is determined based on the detected electrical signal.

By the aforementioned method, since it takes a predetermined time until the reactive state in the vessel in which the mixture of the specimen and the reagent is contained becomes stationary, the presence or absence of the target substance in the specimen cannot be determined until the predetermined time has elapsed.

BRIEF DESCRIPTION OF THE DRAWINGS

FIG. 2 illustrates a detailed structure of a reaction unit according to the first embodiment.

FIG. 6 is a cross-sectional view of the reaction unit when time $t=t_0$, as shown in FIG. 5.

FIG. 7 is a cross-sectional view of the reaction unit from $t_0$ to $t_1$, as shown in FIG. 5.

FIG. 10 is a cross-sectional view of the reaction unit 2 when time $t=t_2$, as shown in FIG. 5.

FIG. 11 is a cross-sectional view of the reaction unit from $t_3$ to $t_4$, as shown in FIG. 5.

FIG. 12 is a cross-sectional view of the reaction unit from $t_4$ to $t_5$, as shown in FIG. 5.

FIG. 13 is a cross-sectional view of the reaction unit from $t_6$ to $t_5$, as shown in FIG. 7.

DETAILED DESCRIPTION

In general, according to one embodiment, a specimen measurement apparatus includes a detector, a reaction promoter and processing circuitry. The detector generates an electrical signal based on a reactive state in a reaction chamber in which a mixture of a test substance and a reagent is contained. The reaction promoter supplies to the reaction chamber energy to promote reaction in the reaction chamber. The processing circuitry switches an energy supply state in accordance with a predetermined time schedule, determines a stationary state of the test substance based on an electrical signal generated after the energy supply state is switched, and outputs the stationary state obtained by the determination.

First Embodiment

A specimen measurement apparatus according to the first embodiment will be explained with reference to the drawings.

Figure 1:
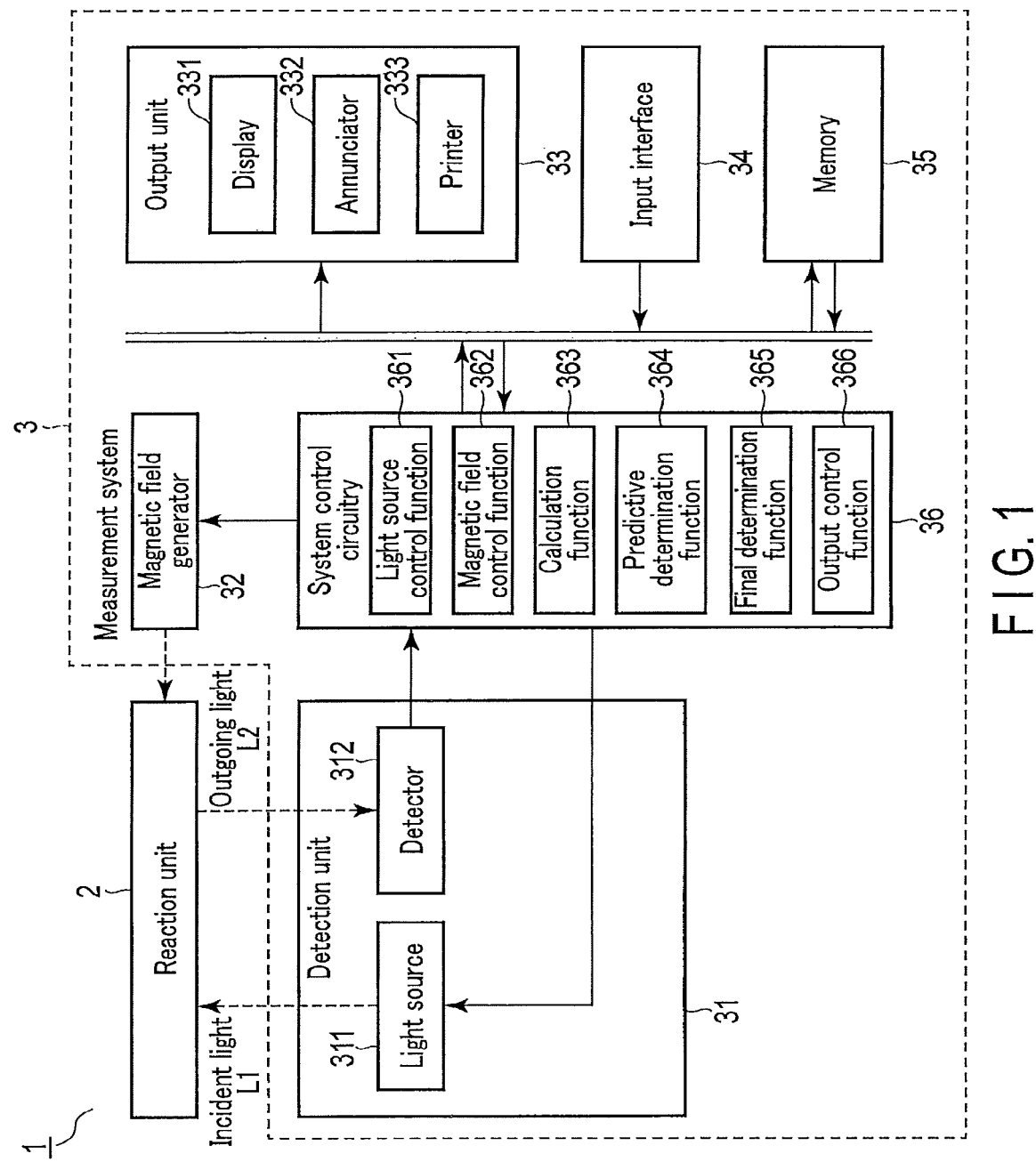
FIG. 1 is a block diagram showing the structure of a specimen measurement apparatus according to the first embodiment.

FIG. 1 is a block diagram showing the structure of a specimen measurement apparatus 1 according to the first embodiment. FIG. 2 shows the detailed structure of a reaction unit 2. As shown in FIG. 1, the specimen measurement apparatus 1 includes the reaction unit 2 and a measurement system 3. The reaction unit 2 is detachable and attachable relative to the specimen measurement apparatus 1.

The reaction unit 2 includes a housing 21, a transparent substrate 22, an optical waveguide 23 and a shield member 24, as shown in FIG. 2. The housing 21 is partially opened at a bottom surface, and a chip in which the optical waveguide 23 and the shield member 24 are formed on the transparent substrate 22 by thin-film technology is inserted into the opened portion. The shield member 24 is partially opened (opened end 24a). A reaction chamber 201 is formed of the housing 21, the optical waveguide 23, and the shield member 24, etc. The reaction unit 2 is capable of containing a sample solution including a test object (test substance) inside thereof, i.e., in the reaction chamber 201.

The housing 21 is made of a resin, etc., for example. A first concave portion is formed on the lower surface of the housing 21. A second concave portion that forms the upper and side surfaces of the reaction chamber 201 is formed in part of the upper surface of the first concave portion. In the first concave portion, the shield member 24, the optical waveguide 23, and the transparent substrate 22 are arranged in this order from above. A hole 21a that extends upward through the housing 21 is formed close to one end of the upper surface of the second concave portion so as to inject a sample solution and a reagent, etc. to the reaction chamber 201, and a hole 21b that extends upward through the housing 21 is formed close to the other end of the upper surface of the second concave portion so as to release air from the reaction chamber 201. A plurality of holes 21a and a plurality of holes 21b may be formed.

The transparent substrate 22 is made of a resin or an optical glass, etc., for example. The transparent substrate 22 allows incident light from a light source 311 provided in the measurement system 3 to pass through and enter the optical waveguide 23. The transparent substrate 22 allows light exited from the optical waveguide 23 to pass through and travel toward a detector 312 provided in the measurement system 3.

The optical waveguide 23 is made of a material that allows light to pass through, such as a resin or an optical glass, etc., for example. For example, a phenol resin, an epoxide resin or an acrylic resin, etc. may be used for the optical waveguide 23. The optical waveguide 23 serves as an optical path of light that enters from the transparent substrate 22 and exits to the transparent substrate 22. That is, the optical waveguide 23 has a function similar to a core (core material) in an optical fiber. The shield member 24 and the transparent substrate 22 are made of a material having a refractive index different from a material of the optical waveguide 23, and have a function as a cladding that entirely reflects light on a boundary surface with respect to the optical waveguide 23, and confines light in the optical waveguide 23. The shield member 24 and the transparent substrate 22 physically protect the optical waveguide 23.

The optical waveguide 23 propagates light entered from the measurement system 3 through the transparent substrate 22. In the optical waveguide 23, light affected by the concentration of the test substance contained in the reaction chamber 201, i.e., the reactive state, is propagated.

A grating 23a is provided at the shield member 24 side close to the part from which light enters the optical waveguide 23. The grating 23a diffracts incident light L1 entered into the optical waveguide 23 at a predetermined angle. The light diffracted by the grating 23a enters a boundary surface between the optical waveguide 23 and the transparent substrate 22, and a boundary surface between the optical waveguide 23 and a surface defined by the shield member 24, or the mixture 202, at an angle equal to or less than a supplementary angle of a critical angle. The incident light L1 is repetitively reflected on the boundary surface of the optical waveguide 23 and propagated (guided) through the optical waveguide 23.

A grating 23b is provided at the shield member 24 side close to the part from which light exits from the optical waveguide 23. The grating 23b diffracts light guided by the optical waveguide 23 at a predetermined angle. The light diffracted by the grating 23b exits from the optical waveguide 23 at a predetermined angle.

The shield member 24 has an opening at the position of the second concave portion of the housing 21. The shield member 24 is arranged in contact with the upper surface of the optical waveguide 23. The shield member 24 is arranged in contact with the upper surface of the optical waveguide 23 to form a plane shield layer. As shown in FIG. 2, the shield member 24 has an opened end 24a to expose the main surface (for example, the upper surface) of the optical waveguide 23. The opened end 24a is a vertical surface that forms an opening inside the shield member 24. The upper surface of the optical waveguide 23 is exposed from the opened end 24a.

The upper surface of the reaction chamber 201 is defined by the upper surface of the second concave portion of the housing 21, the side surfaces are defined by the side surfaces of the second concave portion of the housing 21 and the opened end 24a of the shield member 24, and the lower surface is defined by the upper surface of the optical waveguide 23.

The reaction chamber 201 contains a sample solution and a reagent and allows a test substance included in the sample solution to react with the reagent. A plurality of first antibodies 211 are immobilized at the lower surface of the reaction chamber 201, namely, the upper surface of the optical waveguide 23. The first antibodies 211 are a substance that specifically reacts with antigens 212 included in the test substance by an antigen-antibody reaction. The first antibodies 211 are immobilized on the upper surface of the optical waveguide 23 by hydrophobic interaction or chemical bond, etc., with respect to the upper surface of the optical waveguide 23, for example.

The reaction chamber 201 is initially vacant, for example. When measuring the test substance, mixture 202 of the sample solution and the reagent is injected into the reaction chamber 201 through the hole 21a, for example. The sample solution includes the test substance including antigens 212. The reagent includes reagent components 213. The reagent components 213 include, for example, second antibodies 214 that specifically react with the antigens 212 by antigen-antibody reaction and magnetic particles 215 to which the second antibodies 214 are immobilized. The magnetic particles 215 are made of a material at least part of which is a magnetic substance such as magnetite, etc. The magnetic particles 215 are prepared, for example, by covering the surface of a particle made of a magnetic substance with a high polymer material. The magnetic particles 215 may be prepared by covering the surface of a particle formed of a high polymer material with a magnetic substance. The magnetic particles 215 may be substituted by any substance that can be dispersed into the mixture 202.

By injecting the mixture 202 into the reaction chamber 201, the reaction chamber 201 contains the antigens 212 included in the test substance in the sample solution, and the reagent components 213 included in the reagent, in addition to the first antibodies 211 immobilized on the upper surface of the optical waveguide 23. If the mixture 202 is injected into the reaction chamber 201, air in the reaction chamber 201 is discharged from the hole 21b.

The reagent components 213 can be dispersed in the mixture 202 filed in the reaction chamber 201. The magnetic particles 215 in which the gravitation is greater than the buoyancy applied oppositely to the gravitation in the mixture 202 are adopted in the embodiment. The magnetic particles 215, to which the second antibodies 214 are immobilized, are immobilized close to the upper surface of the optical waveguide 23 by the second antibodies 214 being bonded with the first antibodies 211 via the antigens 212. The second antibodies 214 may be the same as, or different from the first antibodies 211.

In the reaction unit 2, if the first antibodies 211 immobilized on the upper surface of the optical waveguide 23 react with the antigens 212 included in the test substance, the magnetic particles 215 to which the second antibodies 214 are immobilized, are immobilized close to the upper surface of the optical waveguide 23. The light traveled through the optical waveguide 23 is scattered and absorbed by the magnetic particles 215 immobilized close to the upper surface of the optical waveguide 23. As a result, the light traveled through the optical waveguide 23 is attenuated and exits from the optical waveguide 23. That is, the incident light L1 is attenuated in accordance with the amount of antigens 212 that bond the first antibodies 211 to the second antibodies 214 immobilized to the magnetic particles 215, i.e., the number of the antigens 212 contained in the reaction chamber 201.

In the following explanation, an area from the surface of the optical waveguide 23 to the broken line shown in FIG.

2 in the reaction chamber 201, i.e., an area close to the upper surface of the optical waveguide 23, is defined as a sensing area 205.

If the light is propagated within the optical waveguide 23, proximity field light (evanescent light) is generated on the upper surface of the optical waveguide 23. The sensing area 205 is an area where proximity field light may be generated. In the sensing area 205, the first antibodies 211 immobilized on the upper surface of the optical waveguide 23 are bonded with the second antibodies 214 that are immobilized to the magnetic particles 215 included in the reagent components 213 via the antigens 212 included in the test substance in the sample solution. Accordingly, the magnetic particles 215 to which the second antibodies 214 are immobilized are retained close to the upper surface of the optical waveguide 23.

Next, an influence upon the light propagated through the optical waveguide 23 by an antigen-antibody reaction, etc. occurring in the reaction chamber 201 will be explained. The first antibodies 211, the second antibodies 214 and the antigens 212 are extremely smaller than the magnetic particles 215. In FIGS. 2 and 7-13, the first antibodies 211, the antigens 212, the second antibodies 214, and the magnetic particles 215 are illustrated at a similar size to schematically show the combination reaction.

If the magnetic particles 215 enter the sensing area 205, the second antibodies 214 immobilized to the magnetic particles 215 are bonded to the first antibodies 211 immobilized on the upper surface of the optical waveguide 23 via the antigens 212. Accordingly, the magnetic particles 215 to which the second antibodies 214 are immobilized are retained in the sensing area 205. In a state where the magnetic particles 215 are retained in the sensing area 205, if proximity field light is generated on the upper surface of the optical waveguide 23, the magnetic particles 215 in the sensing area 205 scatter and absorb the proximity field light, and attenuate the proximity field light. Scattering and absorbing of the proximity field light in the sensing area 205 affects light propagated through the optical waveguide 23. That is, as the proximity field light is attenuated in the sensing area 205, the light traveling through the optical waveguide 23 is attenuated. Therefore, if the proximity field light is greatly scattered and absorbed in the sensing area 205, the intensity of light propagated through the optical waveguide 23 decreases. In other words, as the amount of the magnetic particles 215 retained in the sensing area 205 becomes greater, the intensity of light output from the optical waveguide 23 decreases.

The magnetic particles 215 retained in the sensing area 205 include the magnetic particles 215 other than those in which the first antibodies 211 immobilized on the upper surface of the optical waveguide 23 are bonded to the second antibodies 214 that are immobilized to the magnetic particles 215 via the antigens 212, which are the measurement target. Accordingly, in order to measure an accurate concentration of the antigens 212 included in the test substance, it is necessary to keep the magnetic particles 215, to which the second antibodies 214 not bonded to the antigens 212 are immobilized, i.e., which should not be counted in measurement, away from the sensing area 205. Specifically, the magnetic particles 215 to which the second antibodies 214 not bonded to the antigens 212 are immobilized may be moved by proximity actions by a magnetic field, for example.

By this method, only the magnetic particles 215, in which the first antibodies 211 immobilized on the upper surface of the optical waveguide 23 are bonded to the second antibodies 214 via the antigens 212, are finally retained in the sensing area 205. Thus, the value of the intensity of light emitted from the reaction unit 2 and the temporal change in intensity correspond to the amount and the concentration, etc. of the magnetic particles 215 retained in the sensing area 205.

The reaction unit 2 may be configured to perform parallel measurement that measures the same test substance for the same measurement item by multiple channels at the same time. In this case, the reaction unit 2 has an independent optical waveguide for each channel, for example.

The measurement system 3 includes a detection unit 31, a magnetic field generator 32, an output unit 33, an input interface 34, a memory 35, and system control circuitry 36, as shown in FIG. 1.

The detection unit 31 includes the light source 311 and the detector 312.

The light source 311 is a diode such as an LED or a lamp such as a xenon lamp, for example. The light source 311 is arranged at a position where light can be applied to the grating 23a in the optical waveguide 23. The light source 311 applies incident light L1 to the optical waveguide 23 through the transparent substrate 22 of the reaction unit 2. The incident light L1 enters the optical waveguide 23 and is diffracted by the grating 23a. The incident light L1 diffracted by the grating 23a is entirely reflected within the optical waveguide 23 and propagated to reach the grating 23b. The light that has reached the grating 23b is diffracted by the grating 23b, and exits from the optical waveguide 23 at a predetermined angle as an outgoing light L2. The light source 311 may be replaced with a source that generates electromagnetic waves, etc., other than light.

The detector 312 is a reactive state signal output unit that outputs an electrical signal based on a reactive state in the reaction chamber 201 in which the mixture 202 is contained. Specifically, the detector 312 detects the outgoing light L2 exiting from the optical waveguide 23, and generates an electrical signal indicating the intensity of the detected outgoing light L2, i.e., digital data concerning detected light intensity. The digital data concerning the detected light intensity generated by the detector 312 is supplied to the system control circuitry 36.

The detection unit 31 may be configured to perform parallel measurement that measures the same test substance for the same measurement item by multiple channels at the same time. In this case, the detection unit 31 may be provided with a light source and a detector for each channel, or may share a light source and a detector for multiple channels.

The magnetic field generator 32 is a reaction promotion unit that generates energy to promote reaction within the reaction chamber 201, i.e., bonding between the second antibodies 214 immobilized to the magnetic particles 215 and the first antibodies 211 immobilized on the upper surface of the optical waveguide 23 via the antigens 212. Specifically, the magnetic field generator 32 has an upper magnetic field generator 32a and a lower magnetic field generator 32b, as shown in FIG. 2. The magnetic field generator 32 also has a driving circuit not shown in the drawings. The magnetic field generator 32 applies a magnetic field to the reaction chamber 201 under control of the system control circuitry 36.

The upper magnetic field generator 32a is formed, for example, of a permanent magnet, and an electromagnet, etc. The upper magnetic field generator 32a is provided at an upper portion of the reaction unit 2, as shown in FIG. 2. The upper magnetic field generator 32a generates a vertically upward magnetic field in the reaction chamber 201, the magnetic field having the same strength relative to the horizontal direction. Due to the generated vertically upward magnetic field, the magnetic particles 215 to which the second antibodies 214 are immobilized receive the vertically upward force and move upward. In this case, the upper magnetic field generator 32a generates a predetermined magnetic field intensity so that the magnetic particles 215 to which the second antibodies 214 are immobilized selectively move away from the sensing area 205. That is, the upper magnetic field generator 32a adjusts the intensity of the magnetic field to be generated so that only the magnetic particles 215, to which the second antibodies 214 bonded to the first antibodies 211 immobilized on the upper surface of the optical waveguide 23 via the antigens 212 are immobilized, are able to be retained in the sensing area 205.

The lower magnetic field generator 32b is formed, for example, of a permanent magnet, and an electromagnet, etc. The lower magnetic field generator 32b is provided at a lower portion of the reaction unit 2. The lower magnetic field generator 32b generates a vertically downward magnetic field, which is energy to promote a reaction in the reaction chamber 201, the magnetic field having the same strength relative to the horizontal direction. Due to the generated vertically downward magnetic field, the magnetic particles 215 to which the second antibodies 214 are immobilized receive the vertically downward force and move downward.

The output unit 33 includes a display 331, an annunciator 332, and a printer 333.

The display 331, for example, may be a general display output device such as a liquid crystal display or an Organic Light Emitting Diode (OLED) display, etc. The display 331 displays various operation screens, information indicating the light intensity of the outgoing light L2 supplied from the detector 312, temporal data of the light intensity, and measurement results of test substance, etc., in accordance with the control of the system control circuitry 36. The measurement results indicate, for example, the concentration, weight, or number, etc. of antigens 212.

The annunciator 332 is, for example, a speaker. The annunciator 332 announces the measurement results, etc. of the test substance to an operator, under the control of the system control circuitry 36.

The printer 333 prints various operation screens, information indicating the light intensity of the outgoing light L2 supplied from the detector 312, temporal data of the light intensity, and measurement results of a test substance, etc. displayed on the display 331, under the control of the system control circuitry 36.

The input interface 34 is implemented, for example, by a trackball, a switch button, a mouse, a keyboard, a touch pad through which an input operation is carried out by touching an operation surface, and a touch panel display with an integrated display screen and touch pad, etc. The input interface 34 outputs an operation input signal in accordance with an operation of the operator to the system control circuitry 36. In the present embodiment, the input interface circuit is not limited to physical operation components such as a mouse and a keyboard. For example, the input interface circuit also includes electrical signal processing circuitry that receives an electrical signal corresponding to an input operation through an external input device separate from the apparatus, and outputs the electrical signal to the system control circuitry 36.

The memory 35, for example, has a processor-readable storage medium, such as a magnetic storage medium, an optical storage medium, or a semiconductor memory. The memory 35 stores a program executed by the circuit of the specimen measurement apparatus 1 according to the present embodiment. A program and data in the storage medium of the memory 35 may be partially or entirely downloaded through an electronic network.

The memory 35 stores information indicating the light intensity of the outgoing light L2 supplied from the detector 312, temporal data of the light intensity, and measurement results of test substance which is a measurement target, etc.

The memory 35 stores setting information for performing measurement of a target test substance. The setting information includes information to set a timing of performing predetermined processing required for measurement, for example. The timing of performing predetermined processing required for measurement may be, for example, a timing when application of a lower magnetic field generated by the lower magnetic field generator 32b is initiated, a timing when a detection section starts, a timing of calculation (a timing when application of the lower magnetic field is stopped), a timing when the detection section ends, a timing when application of a upper magnetic field is initiated, and a timing when a final determination is performed. Information to set the above timings includes a relative elapsed time from a predetermined time, or an absolute time when predetermined processing is executed. The relative elapsed time from a predetermined time or the absolute time when predetermined processing is executed is empirically or experimentally obtained in advance.

The memory 35 stores a predetermined regulation value $T_s$. The regulation value $T_s$ is a regulation value for an accumulated value of a changing rate of light intensity corresponding to the concentration of the test substance. The regulation value $T_s$ is used for determining whether or not there is a high possibility that the measurement results of the test substance indicate a positive.

The memory 35 stores a predetermined threshold value $T_A$. The threshold value $T_A$ is a threshold value for the light intensity corresponding to the concentration of the test substance. The threshold value $T_A$ is used for determining the stationary state of the test substance. The stationary state indicates a degree of a positive or a negative indicated by the measurement results, for example. The threshold value $T_A$ is used for a final determination as to whether or not there is a high possibility that the measurement results of the test substance indicate a positive. The threshold value $T_A$ may be a plurality of step-by-step threshold values. That is, by comparing the light intensity included in the digital data with the plurality of step-by-step threshold values, the determination can indicate more detailed measurement results.

The system control circuitry 36 is, for example, a processor that controls each structural circuit of the specimen measurement apparatus 1. The system control circuitry 36 serves as a central element of the specimen measurement apparatus 1. The system control circuitry 36 reads out each operation program from the memory 35 and executes the program to implement a light source control function 361, a magnetic field control function 362, a calculation function 363, a predictive determination function 364, a final determination function 365, and an output control function 366.

The light source control function 361 is a function of controlling the light source 311 to generate light under a predetermined condition. The system control circuitry 36 executes the light source control function 361 to allow the light source 311 to generate incident light L1 consecutively or intermittently at least for a duration from measurement initiation to measurement termination.

The magnetic field control function 362 is a supply state switch control function of controlling the magnetic field generator 32 in accordance with a time schedule stored in the memory 35 beforehand, and switching the supply state of energy supplied to promote reaction in the reaction chamber 201. Specifically, the system control circuitry 36 executes the magnetic field control function 362 to read setting information from the memory 35, and control the magnetic field generator 32 based on the setting information to generate a magnetic field.

The calculation function 363 is a function of performing various calculations based on digital data of temporal light intensity supplied from the detector 312. The system control circuitry 36 executes the calculation function 363 to perform calculations to obtain an average value of light intensity, a changing rate of light intensity, an accumulated value of the changing rate, etc.

The predictive determination function 364 is a function of performing predictive determination as to whether or not there is a high possibility that the sample solution is a positive, based on the accumulated value of the changing rate of light intensity calculated by the calculation function 363. The predictive determination may be referred to as a pre-determination. With the predictive determination function 364, the system control circuitry 36 reads, for example, a predetermined regulation value $T_s$ from the memory 35. If the accumulated value of the changing rate of light intensity calculated by the calculation function 363 is equal to or less than the regulation value $T_s$, the system control circuitry 36 determines that a possibility is high that the measurement results of the test substance indicate a positive. If the accumulated value of the changing rate of light intensity calculated by the calculation function 363 is greater than the regulation value $T_s$, the system control circuitry 36 determines that a possibility is high that the measurement results of the test substance indicate a weak positive or a negative.

The final determination function 365 is a function of performing a final determination to determine the stationary state of the test substance based on the digital data on the light intensity supplied from the detector 312 during application of an upper magnetic field described later. That is, the final determination function 365 is a function of performing a final determination after the predictive determination is performed by the predictive determination function 364. The final determination by the final determination function 365 may be referred to as a post-determination. With the final determination function 365, the system control circuitry 36 reads setting information and a threshold value $T_A$ from the memory 35. The system control circuitry 36 determines the stationary state of the test substance in accordance with an execution timing included in the read setting information. If the light intensity included in the supplied digital data of temporal light intensity is equal to or less than the threshold value $T_A$, the system control circuitry 36 determines that a possibility is high that the measurement results of the test substance indicate a positive. If the light intensity included in the digital data is greater than the threshold value $T_A$, the system control circuitry 36 determines that a possibility is high that the measurement results of the test substance indicate a weak positive or a negative.

The pre-determination and the post-determination indicate the determination timings by temporal sequence. The determination by the predictive determination function 364 is the pre-determination, and the determination by the final determination function 365 is the post-determination. Accordingly, as explained later, if the final determination by the final determination function 365 is not performed, and the results of the predictive determination by the predictive determination function 364 are to be the results of the final determination, the predictive determination is referred to as a "pre-determination" even though the predictive determination is practically the final determination.

The output control function 366 is a function of controlling the output unit 33 to output the determination results of the stationary state, etc. of the test substance to the operator. With the output control function 366, the system control circuitry 36 controls the display 331 or the printer 333 to present the results of the predictive determination and/or the results of the final determination to the operator. The presentation includes a method of displaying through a display and a method of printing by a printer. The system control circuitry 36 controls the annunciator 332 to report the results of predictive determination and/or the results of final determination to the operator. The report includes a method of reporting by a sound.

Next, the operation of the first embodiment will be described.

Figure 3:
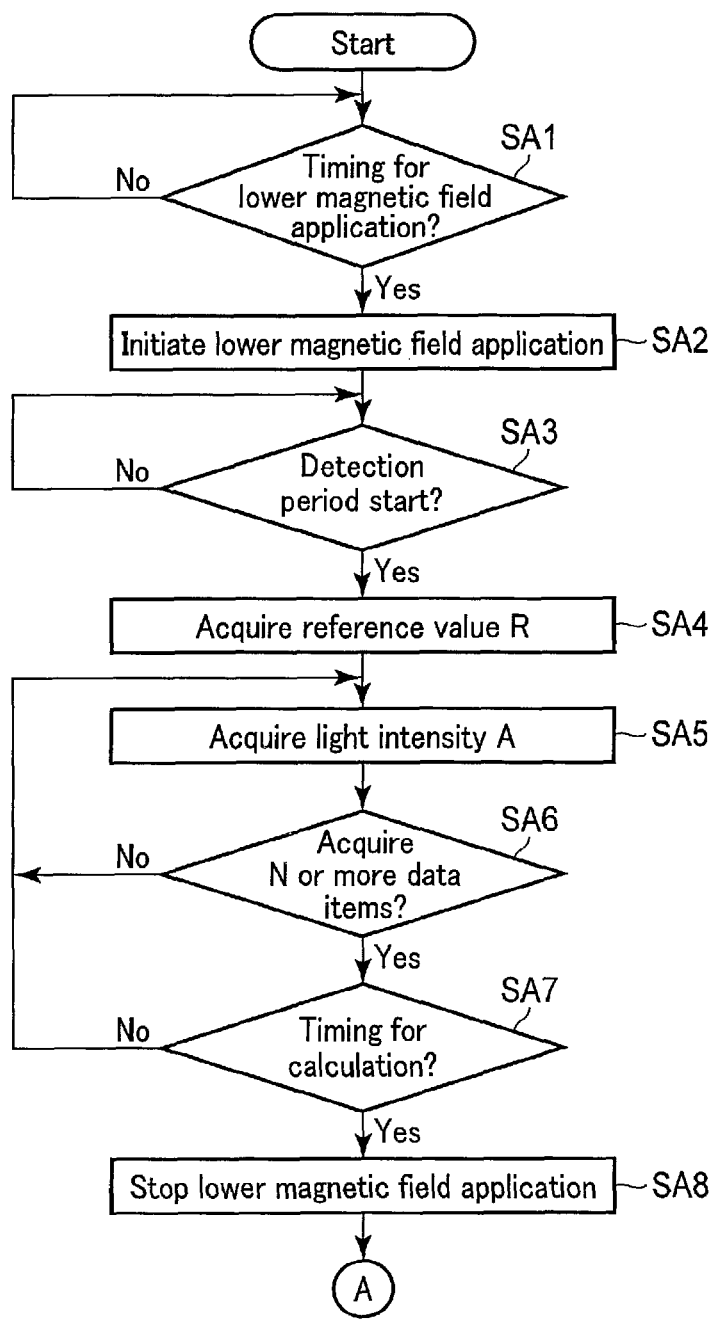
FIG. 3 is an example flowchart illustrating the control operation of a system control circuit according to the first embodiment.
Figure 4:
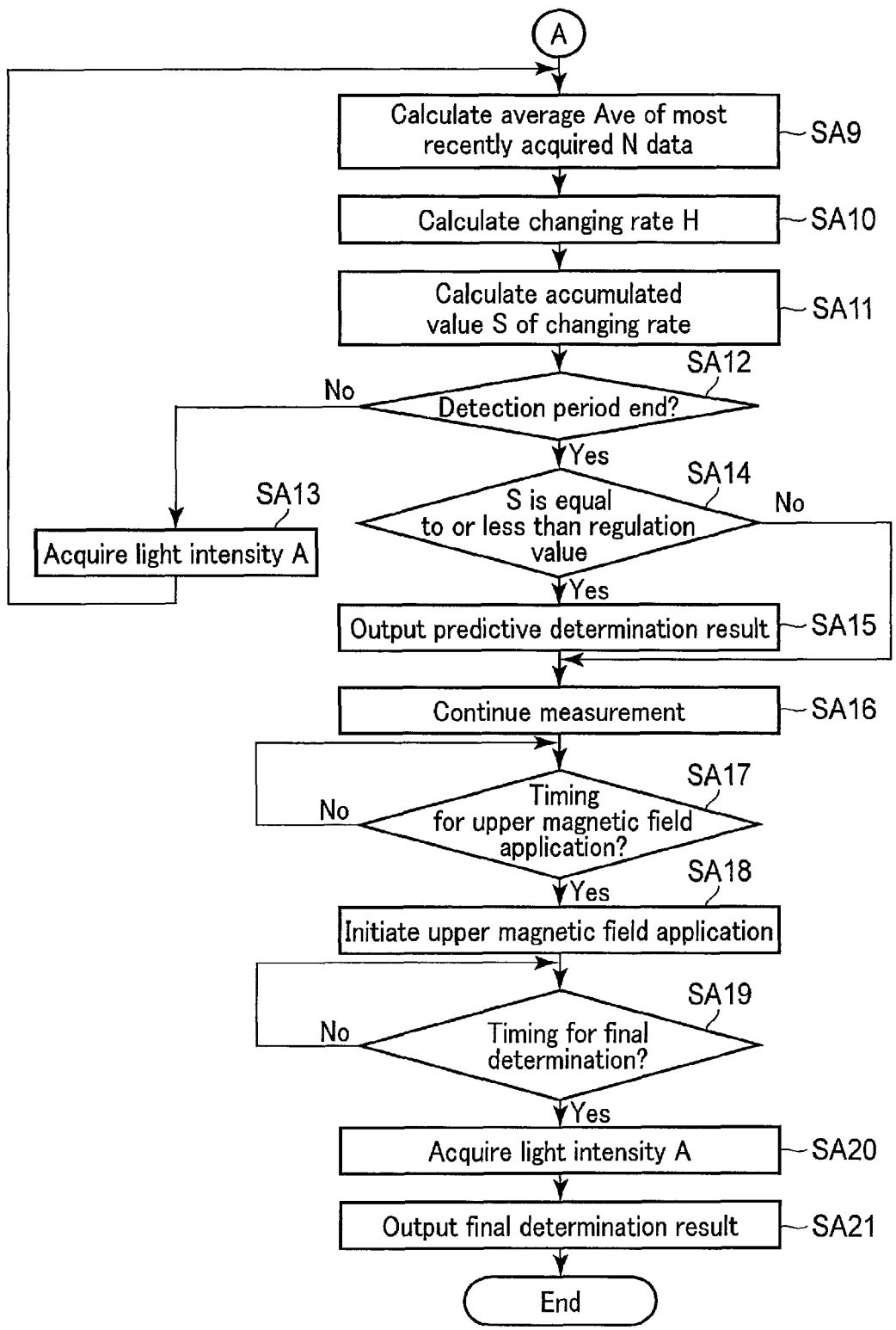
FIG. 4 is an example flowchart illustrating the control operation of a system control circuit according to the first embodiment.
Figure 5:
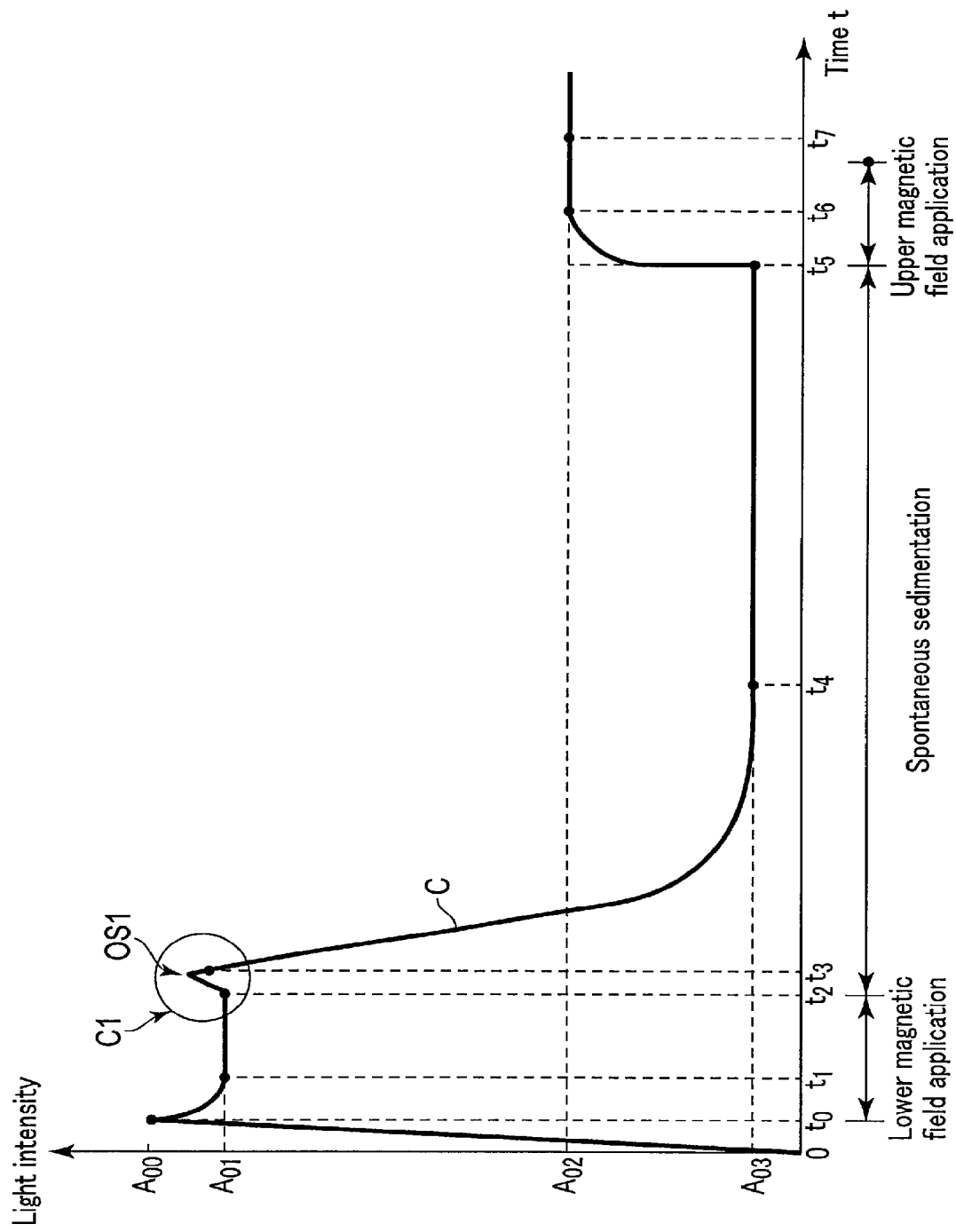
FIG. 5 is a graph showing an example of temporal change of the light intensity of outgoing light.

FIGS. 3 and 4 indicate an example flowchart illustrating the control operation of the system control circuitry 36 according to the first embodiment. FIG. 5 is a graph showing an example of a temporal change of the light intensity of outgoing light L2. In the graph of FIG. 5, the horizontal axis represents time t, and the vertical axis represents the light intensity of outgoing light L2. A curved line in the graph is obtained by plotting temporal change in light intensity A indicated by the digital data acquired based on the reactive state in the reaction unit 2 and output from the detector 312.

First, at time t=0, injection of the mixture 202 including the sample solution and the reagent into the reaction chamber 201 is started. The injection of the mixture 202 to the reaction chamber 201 may be performed automatically or manually.

For example, if the injection of the mixture 202 to the reaction chamber 201 is started, the light source 311 continuously applies light of a certain intensity to the optical waveguide 23. The light emitted from the light source 311 enters the optical waveguide 23 through the transparent substrate 22. The light entered into the optical waveguide 23 is entirely reflected and propagated within the optical waveguide 23, and exits to the detector 312 through the transparent substrate 22. The detector 312 receives the light exiting from the optical waveguide 23 and supplies the data on the light intensity to the system control circuitry 36 at a predetermined time interval.

The system control circuitry 36 determines whether a predetermined elapsed time has passed from time t=0, i.e., whether or not to reach the time $t_0$, which is when the lower magnetic field is applied, based on the predetermined elapsed time included in information that defines, for example, a timing for initiating application of the lower magnetic field (step SA1). The predetermined elapsed time in step SA1 is a time required for the light intensity A to increase from 0 to $A_{00}$. For the period from 0 to $t_0$, the measured light intensity increases. This is because a soluble film including sugar attached on the upper surface of the optical waveguide 23 beforehand to increase preservation stability is dissolved if the reaction chamber 201 is filled with the sample solution and the reagent. The sugar may, for example, be a disaccharide. The system control circuitry 36 may perform determination as to whether or not the time t reaches $t_0$, which is when the lower magnetic field is applied, based on a determination rule predetermined, by observing the temporal change in light intensity successively supplied from the detector 312, for example. The determination rule is a rule that if it is detected that the light intensity is a peak value, it is determined that the time t reaches $t_0$, which is when the lower magnetic field is applied.

If the time t reaches $t_0$, which is when the lower magnetic field is applied (Step SA1: Yes), the system control circuitry 36 controls the magnetic field generator 32 to initiate application of the lower magnetic field (Step SA2). FIG. 6 is a cross-sectional view of the reaction unit 2 when time $t=t_0$, as shown in FIG. 5. As shown in FIG. 6, application of the lower magnetic field is initiated when the time $t=t_0$. In FIG. 6, downward arrows indicate the direction of flux $B_1$ generated due to the application of the lower magnetic field. The flux $B_1$ is formed of a plurality of magnetic force lines b, and in effect passes through the reaction chamber 201 downward.

After the application of the lower magnetic field is initiated, the light intensity is converged to a predetermined value $A_{01}$ when the time t reaches $t_1$. FIG. 7 is a cross-sectional view of the reaction unit from $t_0$ to $t_1$, as shown in FIG. 5. As shown in FIG. 7, the plurality of magnetic particles 215, to which the second antibodies 214 are immobilized in the reaction chamber 201 that is filled with the sample solution, receive a magnetic force in the vertically downward direction by the lower magnetic field, and part of the magnetic particles 215 is drawn by the magnetic force lines b and is started to be aligned along the magnetic force lines b. The magnetic particles 215 to which the second antibodies 214 are immobilized which have been aligned along the magnetic force lines b gradually move down due to gravitation and magnetic forces, and enter the sensing area 205. The second antibodies 214 immobilized to the magnetic particles 215 that have entered the sensing area 205 are bonded to the first antibodies 211 immobilized on the upper surface of the optical waveguide 23 via the antigens 212.

On the other hand, the magnetic particles 215 to which the second antibodies 214 are immobilized that have not been aligned along the magnetic force lines b gradually move down due to gravitation, and enter the sensing area 205. The second antibodies 214 immobilized to the magnetic particles 215 that have entered the sensing area 205 are bonded to the first antibodies 211 immobilized on the upper surface of the optical waveguide 23 via the antigens 212.

From $t_0$ to $t_1$, since the magnetic particles 215 to which the second antibodies 214 are immobilized successively enter the sensing area 205, the light intensity decreases. The light intensity is started to decrease immediately after $t_0$ in a large decrease rate (inclination). The decrease rate of the light intensity becomes lower over time. The decrease rate of the light intensity becomes almost zero at $t_1$. That is, when the time $t=t_1$, the light intensity is converged at the intensity $A_{01}$.

Figure 8:
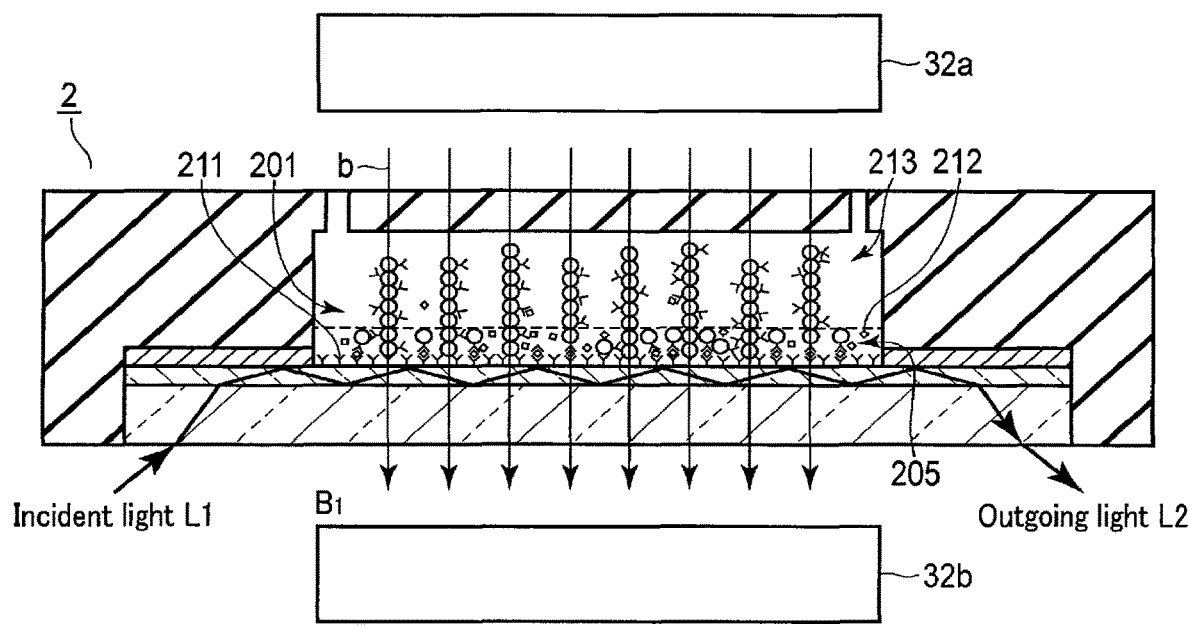
FIG. 8 is a cross-sectional view of the reaction unit from $t_1$ to $t_2$, as shown in FIG. 5.

FIG. 8 is a cross-sectional view of the reaction unit from $t_1$ to $t_5$, as shown in FIG. 2. As shown in FIG. 8, entrance of the magnetic particles 215 to which the second antibodies 214 are immobilized to the sensing area 205 is stopped. Accordingly, the light intensity is converged at the intensity $A_{01}$ when the time $t=t_1$. From $t_1$ to $t_2$, part of the antigens 212 contained in the reaction chamber 201 is successively bonded to the second antibodies 214.

Figure 9:
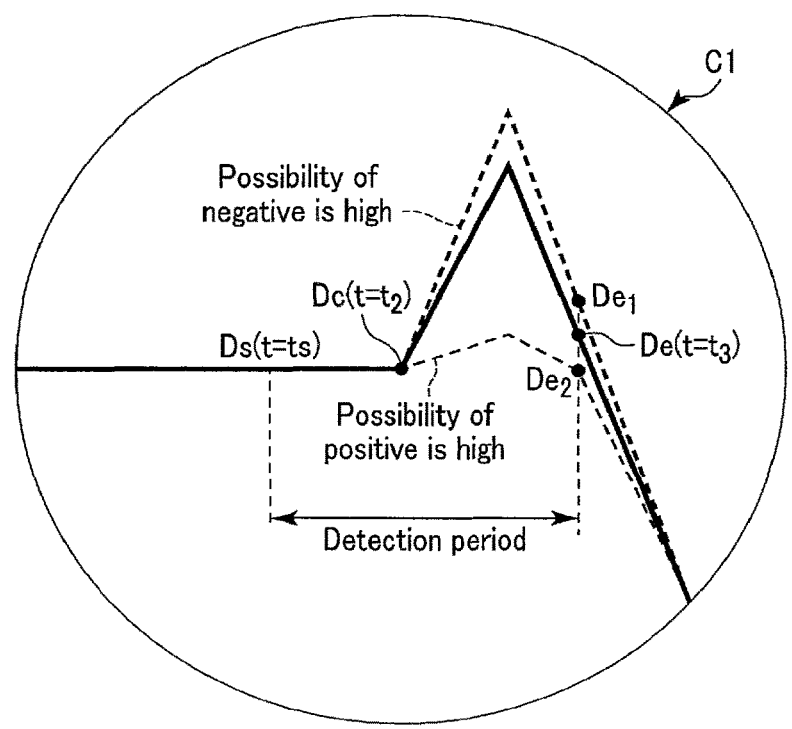
FIG. 9 is an enlarged view of a part of a curved line C in FIG. 5.

FIG. 9 is an enlarged view of a part of a curved line C in FIG. 5. As shown in FIG. 9, in the present embodiment, a period from a start point $D_s$ ($t=t_s$) to an end point $D_e$ ($t=t_3$) within a period from $t_1$ to $t_2$ is referred to as a detection period.

The system control circuitry 36 determines whether a predetermined elapsed time has passed from time $t=0$, which is when application of the lower magnetic field is initiated, namely, whether or not the time reaches $t_s$ (step SA3), based on the predetermined elapsed time included in information that defines, for example, a timing when the detection period starts. The predetermined elapsed time included in information that defines a timing when the detection period starts may be an elapsed time from time 0.

If the time reaches $t_s$, which is when the detection period starts (step SA3: Yes), the system control circuitry 36 acquires a value from the light intensity data continuously supplied from the detector 312 as a reference value R ($=A_{01}$) (step SA4).

After acquisition of the reference value R, the system control circuitry 36 acquires a value of the light intensity $A_n$ (n=1, 2, 3 . . . ) included in the light intensity data successively provided from the detector 312 as a measurement value (step SA5). The system control circuitry 36 may use the reference value R acquired in step SA4 as the measurement value.

After acquisition of the measurement value $A_n$, the system control circuitry 36 determines whether the number of acquired data items of measurement value is three or more (step SA6). If the number of acquired data items of measurement value is less than N (step SA6: No), the processing returns to step SA5, and the system control circuitry 36 acquires a subsequently supplied measurement value.

If the number of acquired data items of measurement value is equal to or greater than N (step SA6: Yes), the system control circuitry 36 determines whether a predetermined elapsed time has passed from $t_0$, which is when application of the lower magnetic field is initiated, namely, whether or not the time reaches $t_2$, based on the predetermined elapsed time included in information that defines a calculation timing, for example (step SA7). The elapsed time in step SA7 is a relative elapsed time from time $t=t_0$, which is when application of the lower magnetic field is initiated similar to the elapsed time in step SA3, and is a time empirically or experimentally obtained in advance. The system control circuitry 36 may set a time when each of (N−1) data items of light intensity among N data items of light intensity that have been most recently acquired exceeds the reference value R as a calculation timing. The predetermined elapsed time included in information that defines a calculation timing may be an elapsed time from time 0.

If the time does not reach $t_2$ (step SA7: No), the processing returns to step SA5, and the system control circuitry 36 acquires a subsequently supplied measurement value.

If the time reaches $t_2$ (step SA7: Yes), the system control circuitry 36 controls the magnetic field generator 32 to stop application of the lower magnetic field (Step SA8).

If the application of the lower magnetic field is stopped, the magnetic particles 215 to which the second antibodies 214 are immobilized start spontaneous sedimentation by being released from binding due to the lower magnetic field. FIG. 10 is a cross-sectional view of the reaction unit 2 when time $t=t_2$, as shown in FIG. 5. As shown in FIG. 10, the state within the reaction chamber 201 immediately after the application of the lower magnetic field is stopped is substantially the same as the state shown in FIG. 8.

As shown in FIGS. 5 and 9, the light intensity A exhibits a spike-wave in which the pattern changes from an increase to a decrease since overshoot OS1 occurs from $t_2$ to $t_3$. Part of the reagent components 213 is separated from the sensing area 205 for a moment, and overshoot OS1 occurs from $t_2$ to $t_3$, as shown in FIGS. 5-9. The time $t_3$ is a time when the occurrence of overshoot OS1 is ended. The time required to end the overshoot OS1 from when the application of the lower magnetic field is stopped is known since the time when the application of the lower magnetic field is stopped is predetermined, and the time is stored in the memory 35 beforehand. The time is used, for example, for determining a predetermined elapsed time from the time when application of the lower magnetic field is stopped. The elapsed time required to end the overshoot OS1 may be determined experimentally in advance.

In addition, as a criteria to determine whether or not there is a high possibility that the sample solution including the test substance that is a measurement target indicates a positive, the degree of overshoot occurred from $t_2$ to $t_3$ can be adopted. For example, the system control circuitry 36 according to the present embodiment determines, by performing a predetermined calculation, that the possibility of a weak positive or a negative is high if an overshoot of a sharp spike shape occurs from the point Dc (t=t2) indicating a calculation timing to the point De1 (t=t3) indicating the end of the detection period. In addition, the system control circuitry 36 determines that the possibility of a positive is high if an overshoot of a gradual spike shape occurs from the point Dc (t=t2) indicating a calculation timing to the point De1 (t=t3) indicating the end of the detection period. Specifically, the system control circuitry 36 calculates an accumulated value of the changing rate of light intensity from $t_2$ to $t_3$, and determines that the possibility of a positive is high if the calculated accumulated value of the changing rate of light intensity is equal to or less than the regulation value $T_s$. The system control circuitry 36 determined that the possibility of a weak positive or a negative is high if the calculated accumulated value of the changing rate of light intensity is greater than the regulation value $T_s$.

The light intensity A decreases from t3 to t4 if an occurrence of noise in overshoot OS1 is ended. FIG. 11 is a cross-sectional view of the reaction unit from $t_3$ to $t_4$, as shown in FIG. 5. As shown in FIG. 11, the magnetic particles 215 to which the second antibodies 214 are immobilized aligned along the magnetic force lines b are released from the binding due to the lower magnetic field so that the aligned state is broken, and the magnetic particles 215 are randomly dropped toward the upper surface of the optical waveguide 23. As shown in FIG. 5, from $t_3$ to $t_4$, since the magnetic particles 215 to which the second antibodies 214 are immobilized successively enter the sensing area 205, the light intensity A decreases at a greater decrease rate. The decrease rate of the light intensity becomes lower over time. The decrease rate of the light intensity becomes almost zero at $t_4$. That is, the light intensity is converged at the intensity $A_{O3}$ at $t_4$.

FIG. 12 is a cross-sectional view of the reaction unit from $t_4$ to $t_5$, as shown in FIG. 5. As shown in FIG. 12, entrance of the magnetic particles 215 to which the second antibodies 214 are immobilized to the sensing area 205 is stopped. Accordingly, the light intensity is converged at the intensity $A_{O3}$ at $t_4$. In this case, part of the magnetic particles 215 to which second antibodies 214 are immobilized, that are in contact with the upper surface of the optical waveguide 23 is specifically bonded to the first antibodies 211 immobilized on the upper surface of the optical waveguide 23 via the antigens 212. Such magnetic particles 215 to which the second antibodies 214 are immobilized are aligned and deposited on the upper surface of the optical waveguide 23. That is, the sensing area 205 is occupied by the magnetic particles 215 to which the second antibodies 214 are immobilized with essentially no clearance. Part of the magnetic particles 215 to which the second antibodies 214 are immobilized, that are not bonded to the first antibodies 211 immobilized on the upper surface of the optical waveguide 23 at $t_4$ is bonded with the first antibodies 211 immobilized on the upper surface of the optical waveguide 23 from $t_4$ to $t_5$.

After application of the lower magnetic field is terminated, the system control circuitry 36 calculates an average value Ave (n) of most recently obtained N data among data on light intensity successively supplied from the detector 312 (step SA9). The calculation is given by:

[Equation 1]

$$Ave(n) = \frac{A_n + A_{n-1} + A_{n-2} + \ldots + A_{n-N+1}}{N} (n \geq N) \tag{1}$$

After the average value Ave (n) of the light intensity is calculated, the system control circuitry 36 calculates a changing rate $H_n$ of the light intensity by using the reference value R obtained at step SA4 and the average value Ave (n) of the light intensity calculated at step SA9 (step SA10). The calculation is given by:

[Equation 2]

$$H_n = 1 - \frac{R}{Ave(n)}\left(\text{if } 1 - \frac{R}{Ave(n)} \geq 0\right), 0\left(\text{if } 1 - \frac{R}{Ave(n)} < 0\right) (n \geq 3) \tag{2}$$

After the changing rate $H_n$ of the light intensity is calculated, the system control circuitry 36 calculates an accumulated value $S_n$ of the changing rate $H_n$ of the light intensity (step SA11). The calculation is given by:

[Equation 3]

$$S_n = H_n + H_{n-1} + H_{n-2} \ldots (n \geq N) \tag{3}$$

After the accumulated value $S_n$ of the changing rate $H_n$ of the light intensity is calculated, the system control circuitry 36 determines whether a predetermined elapsed time has passed from $t_2$, namely, whether or not the time reaches $t_3$, based on the predetermined elapsed time included in information that defines, for example, a timing when the detection period ends (step SA12). The predetermined elapsed time included in information that defines a timing when the detection period ends may be an elapsed time from time 0.

If the time does not reach $t_3$, which is when the detection period ends (step SA12: No), the system control circuitry 36 acquires a subsequently supplied measurement value (step SA13). Thereafter, the system control circuitry 36 proceeds with steps SA9 to SA12.

If the time reaches t3, which indicates the end of the detection period (step SA12: Yes), the system control circuitry 36 compares the calculated accumulated value $S_n$ of the changing rate $H_n$ of the light intensity with the regulation value $T_n$ stored in the memory 35, and determines whether the accumulated value $S_n$ is equal to or less than the regulation value $T_s$ (step SA14).

If it is determined that the accumulated value $S_n$ is equal to or less than the regulation value $T_s$ (step SA14: Yes), the system control circuitry 36 executes the output control function 366 to present or report to the operator through the output unit 33 that the possibility is high that the results of predictive determination of the test substance, which is the measurement target, indicate a positive (step SA15).

After the presentation or reporting to the operator is performed, the system control circuitry 36 continues measurement after $t_3$ (step SA16).

If it is determined that the accumulated value $S_n$ is greater than the regulation value $T_s$ (step SA14: No), the system control circuitry 36 continues measurement after $t_3$, without performing the presentation or reporting of the results of the predictive determination (step SA16).

The system control circuitry 36 determines whether a predetermined elapsed time has passed from t2, i.e., whether or not the time reaches t5, based on the predetermined elapsed time included in information that defines, for example, a timing for initiating application of the upper magnetic field (step SA17). The predetermined elapsed time included in information that defines a timing for initiating application of the upper magnetic field may be an elapsed time from time 0.

If the time reaches t5, which is when the upper magnetic field is applied (step SA17: Yes), the system control circuitry 36 controls the magnetic field generator 32 to initiate application of the upper magnetic field (step SA18).

Immediately before $t_5$, the magnetic particles 215 to which the second antibodies 214 are immobilized are aligned and deposited on the upper surface of the optical waveguide 23. In this case, most of the magnetic particles 215 to which second antibodies 214 are immobilized, that are in contact with the upper surface of the optical waveguide 23 are specifically bonded to the first antibodies 211 immobilized on the upper surface of the optical waveguide 23.

FIG. 13 is a cross-sectional view of the reaction unit from $t_6$ to $t_5$, as shown in FIG. 7. In FIG. 13, upward arrows indicate the direction of flux $B_2$ generated due to the application of the upper magnetic field. The flux $B_2$ is formed of a plurality of magnetic force lines b, and passes through the reaction chamber 201 in an essentially upward direction. As shown in FIG. 13, the light intensity A is converged at $A_{O2}$ since entrance of the magnetic particles 215 to which the second antibodies 214 are immobilized to the sensing area 205 is stopped.

If the light intensity A is converged at $A_{O2}$, the sensing area 205 only includes the magnetic particles 215 to which the second antibodies 214 are immobilized that are specifically bonded with the first antibodies 211 immobilized on the upper surface of the optical waveguide 23, as shown in FIG. 13.

After initiating the application of the upper magnetic field, the system control circuitry 36 determines whether a predetermined elapsed time has passed from t5, i.e., whether or not the time has reached t7, based on the predetermined elapsed time included in information that defines, for example, a timing for performing final determination (step SA19). The predetermined elapsed time included in information that defines a timing for performing final determination may be an elapsed time from time t=0.

After the application of the lower magnetic field is stopped, if the time reaches a timing for finally determining the stationary state of the test substance after the reaction in the reaction chamber 201 is converged, namely, if the time reaches $t_7$ which is when the final determination function 365 is performed (step SA19: Yes), the system control circuitry 36 performs the final determination function 365 and acquires a value A02 of light intensity data after convergence, supplied continuously from the detector 312.

The system control circuitry 36 executes the final determination function 365, and compares the acquired value A02 of light intensity data with the threshold value $T_A$ stored in the memory 35, and accordingly performs the final determination. The system control circuitry 36 executes the output control function 366, and presents or reports the results of the final determination to the operator through the output unit 33 (step SA21). The system control circuitry 36 may also display the results of the predictive determination at the same time as displaying the results of the final determination on the same display, etc. The system control circuitry 36 may add to the results of the predictive determination an identifier, for example, "*", by which the results of the predictive determination and the final determination can be clearly distinguished, and may display or print the results.

According to the first embodiment, the detector 312 outputs an electrical signal based on the reactive state in the reaction chamber 201 in which the mixture 202 is contained. The system control circuitry 36 controls the magnetic field generator 32 in accordance with a predetermined schedule to apply or stop applying the lower magnetic field to the reaction unit 2. The system control circuitry 36 determines the stationary state of the test substance based on an electrical signal output from the detector 312 after the application of the lower magnetic field is stopped. The system control circuitry 36 outputs the stationary state obtained by the determination. Accordingly, the specimen measurement apparatus can report the determination results of the test substance to the operator before the final determination is performed. Thus, the operator can recognize the stationary state of the test substance before the final determination is performed, and undertake preparation for the next treatment based on the recognized stationary state earlier.

According to the first embodiment, the specimen measurement apparatus 1 that is capable of improving the operation work flow can be provided.

According to the first embodiment, the system control circuitry 36 calculates an accumulated value $S_n$ of the changing rate $H_n$ of the light intensity in a predetermined detection period in which overshoot OS1 occurs. If it is determined that the accumulated value $S_n$ is equal to or less than the regulation value $T_s$, the system control circuitry 36 determines that the possibility is high that the results of the predictive determination of the test substance indicate a positive. By this operation, it is possible to decrease the influence of a current noise, etc. that randomly occurs during measurement.

In addition, according to the first embodiment, the system control circuitry 36 controls the output unit 33 to present or print the results of the predictive determination before the final determination is performed. By this operation, the operator can recognize the results of the predictive determination of the test substance before the final determination is performed.

Furthermore, according to the first embodiment, the system control circuitry 36 controls the output unit 33 to present or print the results of the predictive determination to which an identifier that is clearly distinguishable from the results of the final determination is added. By this operation, the operator can easily recognize whether the presented or printed measurement results are obtained by the predictive determination or the final determination.

[Modification]

In the first embodiment, in the case where the determination results of the predictive determination indicate the high possibility of a positive, after presenting or reporting the results of the predictive determination, the measurement is continued, and the final determination is performed. In this modification, in the case where the predictive determination is performed, and the determination results indicate a high possibility of a positive, a message is displayed to an operator to suggest an input operation to determine suspending measurement at $t_3$ and later after outputting or reporting the results of the predictive determination. If an input suspending measurement is received, measurement is not performed after $t_3$, and the results of the predictive determination are output or reported as the results of the final determination, without performing the final determination.

According to the modification, a specimen measurement apparatus 1A includes a reaction unit 2 and a measurement system 3A.

The measurement system 3A includes a detection unit 31, a magnetic field generator 32, an output unit 33, an input interface 34, a memory 35, and a system control circuitry 36A.

The system control circuitry 36A is a processor that controls each structural circuit of the specimen measurement apparatus 1A, for example. The system control circuitry 36A serves as a central element of the specimen measurement apparatus 1A. The system control circuitry 36A reads out each operation program from the memory 35 and executes the program to implement a light source control function 361, a magnetic field control function 362A, a calculation function 363, a predictive determination function 364, a final determination function 365A, and an output control function 366A.

The magnetic field control function 362A is a function of controlling the magnetic field generator 32 to generate a magnetic field under a predetermined condition. The system control circuitry 36A executes the magnetic field control function 362A to read setting information from the memory 35, and to direct the magnetic field generator 32 to generate a magnetic field based on the setting information. If an input operation for suspending the measurement is received from the operator through the input interface 34, the system control circuitry 36A suspends processing to be performed after $t_3$, namely, stops the application of the upper magnetic field.

The final determination function 365A is a function of performing a final determination to determine a stationary state of the test substance based on the digital data on the light intensity supplied from a detector 312 during application of an upper magnetic field. With the final determination function 365A, the system control circuitry 36A reads setting information and a threshold value $T_A$ from the memory 35. The system control circuitry 36 determines the stationary state of the test substance in accordance with an execution timing included in the read setting information. If the light intensity included in the supplied digital data of light intensity over time is equal to or less than the threshold value $T_A$, the system control circuitry 36A determines that there is a high possibility that the measurement results of the test substance indicate a positive. If the light intensity included in the digital data is greater than the threshold value $T_A$, the system control circuitry 36A determines that a possibility is high that the measurement results of the test substance indicate a weak positive or a negative. If an input operation to suspend the measurement is received from the operator through the input interface 34, the system control circuitry 36A suspends processing to be performed after $t_3$, namely, stops performing the final determination.

The output control function 366A is a function of controlling the output unit 33 to output the determination results, etc. to the operator. The system control circuitry 36A executes the output control function 366A to control the display 331 to present the results of predictive determination or the results of final determination to the operator. The system control circuitry 36 controls the annunciator 332 to report the results of predictive determination or the results of final determination, etc. to the operator. The report includes a method of reporting by a sound, etc. The system control circuitry 36A controls the printer 333 to print the results of predictive determination or the final determination, etc. If the possibility that the results of the predictive determination indicate a positive is high, the system control circuitry 36A controls the display 331 to display a button to accept an input operation of the operator to suspend the measurement after $t_3$. If the input operation indicating the suspension of measurement is received from the operator through the input interface 34, the system control circuitry 36A outputs the results of the predictive determination as the results of the final determination.

Next, the operation of the modification will be described.

Figure 14:
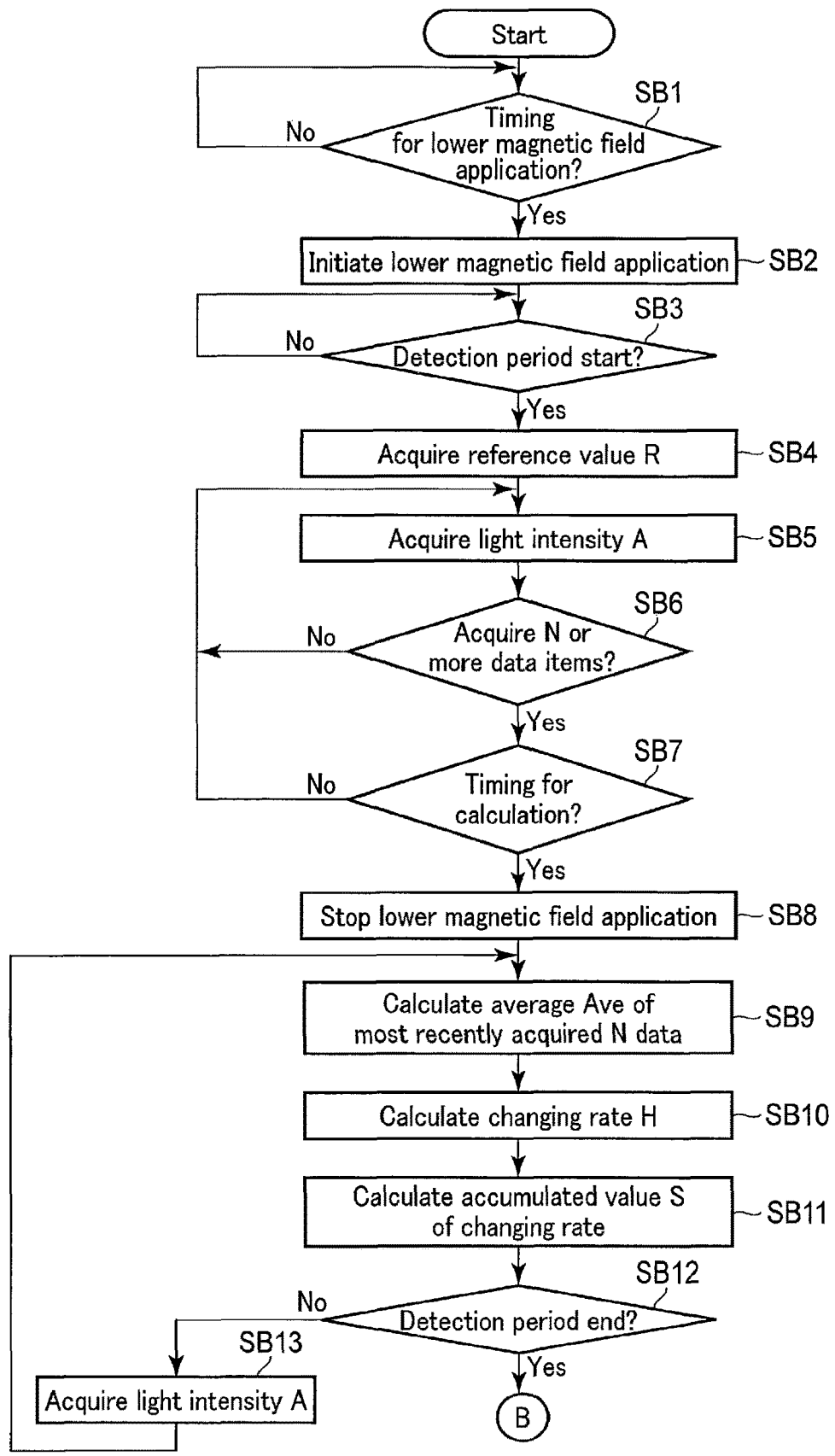
FIG. 14 is an example flowchart illustrating the control operation of a system control circuit according to a modification.
Figure 15:
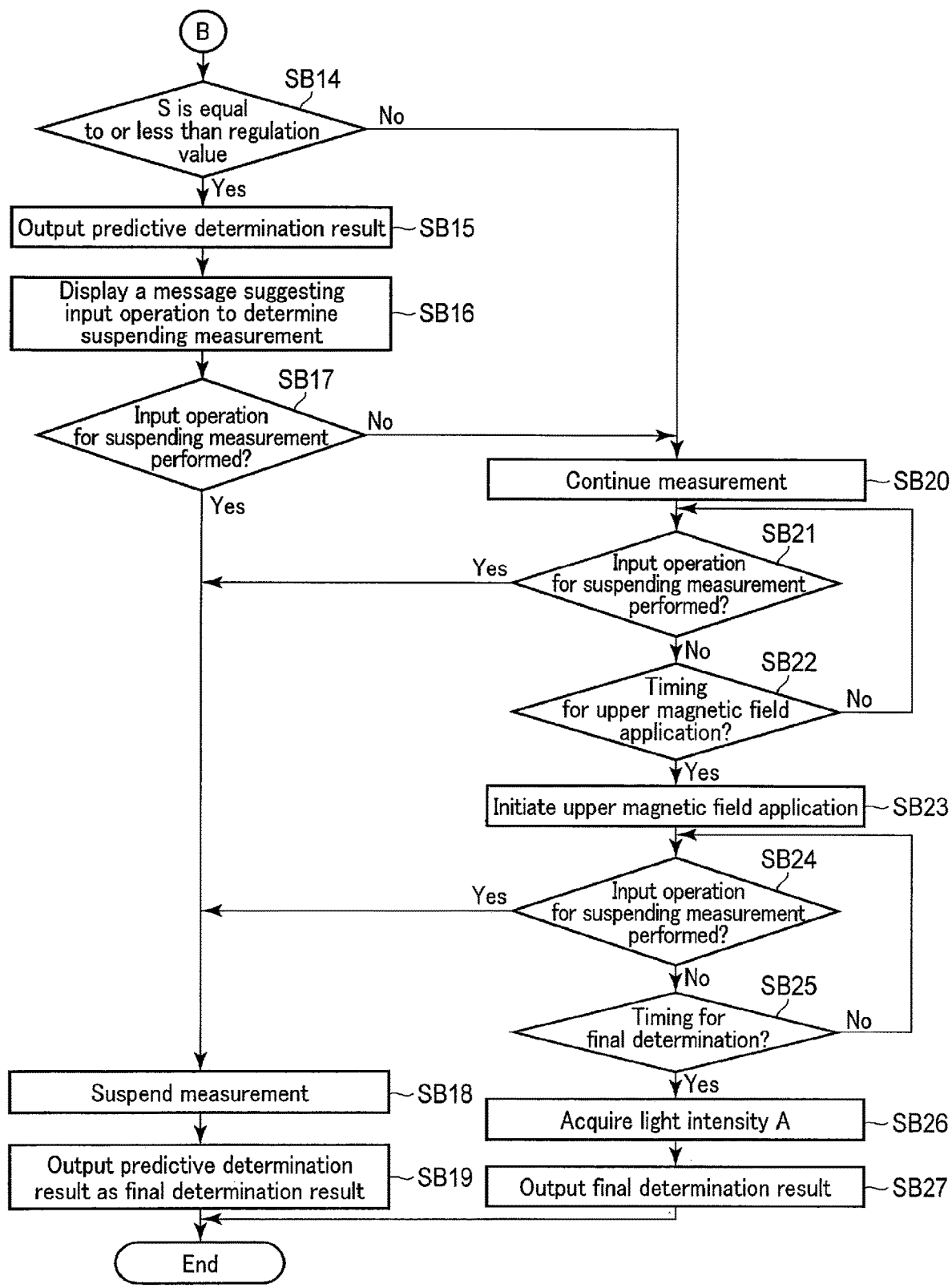
FIG. 15 is an example flowchart illustrating the control operation of a system control circuit according to the modification.

FIGS. 14 and 15 indicate an example flowchart illustrating the control operation of the system control circuit 36A according to the modification. Steps SB1 to SB14 are similar to steps SA1 to SA14 as shown in FIGS. 3 and 4. Accordingly, only steps SB15 to SB27 will be explained below.

If it is determined that the accumulated value $S_n$ is equal to or less than the regulation value $T_s$ (step SB14: Yes), the system control circuitry 36A executes the output control function 366A to present or report to the operator through the output unit 33 that the possibility is high that the results of predictive determination of the test substance, which is the measurement target, indicate a positive (step SB15).

If it is determined that the accumulated value $S_n$ is greater than the regulation value $T_s$ (step SB14: No), the system control circuitry 36A continues measurement after $t_3$, without performing presentation or reporting of the results of the predictive determination (step SB20).

After the presentation or reporting is performed, the system control circuitry 36A executes the output control function 366 to display a button to accept an input operation of the operator to suspend the measurement after $t_3$ through the display 331 (step SB16).

The system control circuitry 36A determines whether the input operation of determining the suspension of the measurement is performed by the operator through the input interface 34 (step SB17).

If the input operation to determine the suspension of measurement is performed by the operator (step SB17: Yes), the system control circuitry 36A suspends measurement in response to the input operation (step SB18). That is, the final determination by the final determination function 365 is not performed.

After the measurement is suspended at step SB18, the system control circuitry 36A executes the output control function 366, and outputs the results of the predictive determination as the results of the final determination through the output unit 33 (step SB19). In this case, with regard to a channel different from a channel that has output the results of the predictive determination indicating the high possibility of a positive, the measurement results are not output since the determination is unconfirmed. The system control circuitry 36A may add to the results of the predictive determination an identifier, for example, "*", by which the results of the predictive determination and the final determination can be clearly distinguished, and display or print the results.

If the input operation to determine the suspension of measurement is not performed by the operator (step SB17: No), the system control circuitry 36A continues measurement after $t_3$ (step SB20).

The system control circuitry 36A determines whether the input operation of determining the suspension of the measurement is performed by the operator through the input interface 34 (step SB21).

If the input operation to determine the suspension of measurement is performed by the operator (step SB21: Yes), the system control circuitry 36A suspends measurement in response to the input operation (step SB18). If the results of the predictive determination are not output at step SB15 (step SB14: No), the system control circuitry 36A proceeds with step SB22 without suspending the measurement even if the input operation of determining the suspension of the measurement is performed by the operator. For simultaneous parallel measurement for multiple channels, for example, if the results of the predictive determination are output through another channel, the measurement may be suspended (step SB18).

If the input operation of determining the suspension of measurement is not performed by the operator (step SB21: No), the system control circuitry 36A determines whether a predetermined elapsed time has passed from t2, i.e., whether or not the time reaches t5, based on the predetermined elapsed time included in information that defines, for example, a timing for initiating application of the upper magnetic field (step SB22).

If the time reaches $t_5$, which is when the upper magnetic field is applied (step SB22: Yes), the system control circuitry 36A controls the magnetic field generator 32 to initiate application of the upper magnetic field (step SB23).

If the time does not reach $t_5$, which is when the upper magnetic field is applied (step SB22: No), the system control circuitry 36A determines whether the input operation of determining the suspension of the measurement is performed by the operator through the input interface 34 (step SB21).

After initiation of application of the upper magnetic field, the system control circuitry 36A determines whether the input operation of determining the suspension of the measurement is performed by the operator through the input interface 34 (step SB24).

If the input operation to determine the suspension of measurement is performed by the operator (step SB24: Yes), the system control circuitry 36A suspends measurement in response to the input operation (step SB18). If the results of the predictive determination are not output at step SB15 (step SB14: No), the system control circuitry 36A proceeds with step SB25 without suspending the measurement even if the input operation of determining the suspension of the measurement is performed by the operator. For simultaneous parallel measurement for multiple channels, for example, if the results of the predictive determination are output through another channel, the measurement may be suspended (step SB18).

If the input operation of determining the suspension of measurement is not performed by the operator (step SB24: No), the system control circuitry 36A determines whether a predetermined elapsed time has passed from t5, i.e., whether or not the time reaches t7, based on the elapsed time included in information that defines, for example, a timing when the final determination is performed (step SB25).

If the time does not reach $t_7$ (step SB25: No), the system control circuitry 36A determines again whether the input operation of determining the suspension of the measurement is performed by the operator through the input interface 34 (step SB21).

If the time reaches $t_7$ (step SB25: Yes), the system control circuitry 36A executes the final determination function 365A and acquires a value $A_{O2}$ of the light intensity data after convergence, continuously supplied from the detector 312.

The system control circuitry 36A executes the final determination function 365A, and compares the acquired value $A_{O2}$ of light intensity data with the threshold value $T_A$ stored in the memory 35, and accordingly performs the final determination. The system control circuitry 36A executes the output control function 366A, and presents or reports the results of the final determination to the operator through the display 331 or the annunciator 332 (step SB27). The system control circuitry 36A may also display the results of the predictive determination at the same time as displaying the results of the final determination on the same display, etc. The system control circuitry 36 may add to the results of the predictive determination an identifier, for example, "*", by which the results of the predictive determination and the final determination can be clearly distinguished, and display or print the results.

According to the modification, if the input operation of determining the suspension of measurement is performed by the operator through the input interface 34, the system control circuitry 36A stops execution of the final determination. By this operation, the operator can select using the measurement results of the predictive determination as the measurement results of the final determination in accordance with the measurement state, thereby reducing the measurement time.

According to the modification, the flow explained with reference to FIGS. 14 and 15 can be simplified. For example, in steps SB14 and onward as shown in FIG. 15, the processing for the input operation, etc. (steps SB15 to SB17, SB21 and SB24) may be omitted. In this case, the results of the final determination may be output automatically (step SB19, step SB27).

Specifically, at step SB14 shown in FIG. 15, if it is determined that the accumulated value $S_n$ is equal to or less than the regulation value $T_s$ (step SB14: Yes), steps SB15 to SB17 are omitted, and the system control circuitry 36A immediately suspends measurement (step SB18). The system control circuitry 36A outputs the results of the predictive determination as the results of the final determination (step SB19).

If it is determined that the accumulated value $S_n$ is greater than the regulation value $T_s$ (step SB14: No), step SB21 is omitted, and if the time reaches $t_5$, which is when the upper magnetic field is applied (step SB22: Yes), the system control circuitry 36A controls the magnetic field generator 32 to apply the upper magnetic field (step SB23). Step SB24 is omitted, and if the time reaches $t_7$ (step SB25: Yes), the system control circuitry 36A executes the final determination function 365A and acquires a value $A_{O2}$ of the light intensity data after convergence, continuously supplied from the detector 312. The system control circuitry 36A outputs the results of the final determination based on the value $A_{O2}$ of the light intensity data after convergence (step SB27).

By the aforementioned simplification, the results of the predictive determination by the predictive determination function 364, namely, the results of the pre-determination, can be automatically output as the results of the final determination. As a result, the need to perform the post-determination which requires more time than the pre-determination can be eliminated.

By the aforementioned simplification, if the predictive determination can be performed, the results of the predictive determination are immediately output as the results of the final determination. In other words, the determination results obtained by the predictive determination are not output as the results of the predictive determination. Accordingly, the measurement can be expedited without necessitating execution of the post-determination.

Other Embodiments

The embodiments described above are not restrictive. For example, in the first embodiment and the modification, the accumulated value $S_n$ of the changing rate $H_n$ of the light intensity obtained in the detection period is used for determining whether the measurement results indicate a high possibility of a positive. However, an inclination or an accumulated value of the light intensity obtained in the detection period may be used for the determination. By adopting the inclination, integrated value, or accumulated value of the light intensity, the predictive determination can be performed with a low calculation load.

The term "processor" used in the above explanation means, for example, circuitry such as a CPU (Central Processing Unit), a GPU (Graphics Processing Unit), an ASIC (Application Specific Integrated Circuit), or a programmable logic device (for example, an SPLD (Simple Programmable Logic Device), a CPLD (Complex Programmable Logic Device), or an FPGA (Field Programmable Gate Array)). The processor implements a function by loading and executing a program saved in storage circuitry. Instead of storing a program on the memory circuitry, the program may be directly integrated into the circuitry of the processor. In this case, the function is realized by reading and executing the program integrated into the circuitry. Each processor of the first embodiment and modification is not limited to a case where each processor is configured as single circuitry; a plurality of independent circuits may be combined into one processor to realize the function of the processor. Furthermore, a plurality of constituent elements shown in FIG. 1 may be integrated into one processor to realize the function.

While certain embodiments have been described, these embodiments have been presented by way of example only, and are not intended to limit the scope of the embodiments. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

The invention claimed is:

1. A specimen measurement apparatus comprising:
a detector configured to generate electrical signals based on a reactive state within a reaction chamber in which a mixture of a test substance and a reagent is contained;
a reaction promoter configured to supply energy to the reaction chamber, to promote reaction in the reaction chamber; and
a processing circuitry configured to:
switch an energy supply state of the energy in accordance with a time schedule, the time schedule including a point in time when supplement of the energy is stopped;
determine a predictive stationary state of the test substance based on a shape of a light intensity spike formed by the electrical signals generated during a time period after the point in time; and
output the predictive stationary state obtained by the determination.

2. The specimen measurement apparatus according to claim 1, wherein the detector is configured to detect light relating to the reactive state in the reaction chamber and generate the electrical signals based on the detected light.

3. The specimen measurement apparatus according to claim 2, wherein the detector is configured to detect light propagated through an optical waveguide provided as a surface of the reaction chamber, and generate the electrical signal based on an intensity of the light in accordance with the reactive state of the reaction chamber.

4. The specimen measurement apparatus according to claim 3, wherein the processing circuitry is configured to receive the electrical signals generated after the point in time, and determine the predictive stationary state of the test substance based on an angle of the light intensity spike obtained from the electrical signals, with respect to a regulation value.

5. The specimen measurement apparatus according to claim 3, wherein the processing circuitry is configured to receive the electrical signals generated after the point in time, and determines the predictive stationary state of the test substance based on an integrated value of intensity of the electrical signals forming the light intensity spike, with respect to a regulation value.

6. The specimen measurement apparatus according to claim 3, wherein the processing circuitry is configured to receive the electrical signals generated after the point in time, and to determine the predictive stationary state of the test substance based on an accumulated value of a changing rate of intensity of the electrical signals forming the light intensity spike, with respect to a regulation value.

7. The specimen measurement apparatus according to claim 1, wherein the processing circuitry is configured to:
determine the predictive stationary state of the test substance as a final determination, if a period in which a reaction in the reaction chamber is converged has passed after the point in time; and
output the determined predictive stationary state before the final determination.

8. The specimen measurement apparatus according to claim 7, wherein the processing circuitry is configured to not execute the final determination if an instruction is input in response to the output of the determined predictive stationary state.

9. The specimen measurement apparatus according to claim 8, wherein the processing circuitry is configured to output the determined predictive stationary state which has been determined as the final determination.

10. The specimen measurement apparatus according to claim 9, wherein the processing circuitry is configured to output the determined predictive stationary state in such a manner that the determined predictive stationary state is identified as the final determination.

11. The specimen measurement apparatus according to claim 7, wherein the processing circuitry is configured to output the determined predictive stationary state and the final determination to be distinguished from each other.

12. The specimen measurement apparatus according to claim 1, wherein the reaction promoter is configured to apply a magnetic field to the reaction chamber.

13. The specimen measurement apparatus according to claim 1,
wherein the reaction promoter is configured to apply a magnetic field to the reaction chamber, and the processing circuitry is configured to determine the predictive stationary state of the test substance based on the electrical signals output after the application of the magnetic field is stopped.

14. The specimen measurement apparatus according to claim 1, wherein the stationary state of the test substance indicates a degree of a positive or a negative indicated by a measurement result of the test substance.

15. The specimen measurement apparatus according to claim 8, wherein the instruction is an instruction to suspend measurement of the test substance.

16. The specimen measurement apparatus according to claim 1, wherein the processing circuitry is configured to output the predictive stationary state obtained by the determination if the electrical signals satisfy a predetermined condition.

17. The specimen measurement apparatus according to claim 6, wherein the processing circuitry is configured to output the predictive stationary state obtained by the determination if the accumulated value is equal to or less than the regulation value.

18. The specimen measurement apparatus according to claim 1, wherein the processing circuitry is configured to perform measurement and processing to determine a final stationary state, after the output of the predictive stationary state.

* * * * *